United States Patent [19]

Sunagawa et al.

[11] Patent Number: 5,310,897

[45] Date of Patent: May 10, 1994

[54] BETA-LACTAMS AND THEIR PRODUCTION

[75] Inventors: Makoto Sunagawa; Akira Sasaki; Koshiro Goda, all of Osaka, Japan

[73] Assignee: Sumitomo Pharmaceuticals Co., Ltd., Osaka, Japan

[21] Appl. No.: 974,302

[22] Filed: Nov. 10, 1992

Related U.S. Application Data

[63] Continuation of Ser. No. 696,110, May 6, 1991, abandoned, which is a continuation-in-part of Ser. No. 358,536, May 26, 1989, abandoned, which is a continuation of Ser. No. 813,723, Dec. 27, 1985, abandoned.

[30] Foreign Application Priority Data

Dec. 27, 1984 [JP] Japan .................. 59-279452
Jul. 4, 1985 [JP] Japan .................. 60-147214

[51] Int. Cl.$^5$ .................................... C07D 487/04
[52] U.S. Cl. ............................. 540/302; 540/350
[58] Field of Search .......................... 540/302, 350

[56] References Cited

U.S. PATENT DOCUMENTS 3,950,357 4/1976 Kahan et al. ................... 540/350
4,350,631 9/1982 Christensen et al. ............ 540/350

FOREIGN PATENT DOCUMENTS 0010317 4/1980 European Pat. Off. ......... 540/302
0071908 2/1983 European Pat. Off. ......... 540/302
188816 7/1986 European Pat. Off. ......... 540/350
2949269 6/1981 Fed. Rep. of Germany ...... 540/350
58-144386 8/1983 Japan ............................. 540/350

OTHER PUBLICATIONS

Journal of American Chemical Society, 100, p. 313 (1978).
Heterocycles, vol. 21, No. 1 (1984) pp. 29–40.
von Riccardo Scartazzini et al., (1974), Helvetica Chimica Acta (vol. 2) Fasc. 7, 1919–1924.
von Riccardo Scartazzini et al., (1973), Helvetica Chimica Acta (vol. 58, Fasc. 8), 2437–2441 (1975).
Schmitt et al. (1980) *J. Org. Chem.*, 45 (6) 1142–1145.
Smith et al. (1981) *Journal of Pharmaceutical Sciences* 70 (3) 272–276.
Farina et al. (1989) *J. Org. Chem.* 54:4962–4966.
Sowinn et al. (1988) *J. Org. Chem.*, 53:4154–4156.
Heterocycles, vol. 21, No. 1 (1984), pp. 29–40.
Recent Advances in the Chemistry of Beta-Lactam Antibiotics, 3rd Edition, pp. 86–99 (1985).
Tetrahydron Letters, vol. 30, pp. 1345–1348 (1989).
Hine, Physical Organic Chemistry pp. 242–243 (1962).
Hutanaka, Tet Letters, 22 3883 (1981).
Hutanaka, Tet Letter 22, 2387 (1984).

*Primary Examiner*—Robert Gerstl
*Attorney, Agent, or Firm*—Birch, Stewart, Kolasch & Birch

[57] ABSTRACT

A beta-lactam compound of the formula:

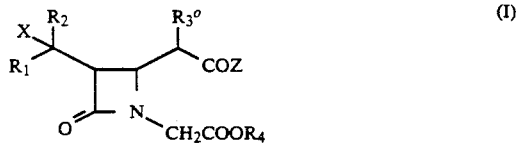

wherein $R_1$ and $R_2$ are, the same or different, each a hydrogen atom or a lower alkyl group, $R_3^0$ is a hydroen atom or a lower alkyl group having a beta-configuration, $R_4$ is a carboxyl-protecting group, X is a hydrogen atom or a protected hydroxyl group and COZ is a protected thiolcarboxyl group, which is useful as a valuable intermediate in the stereospecific production of 1-alkyl-carbapenem compounds.

20 Claims, No Drawings

BETA-LACTAMS AND THEIR PRODUCTION

This application is a continuation of application Ser. No. 07/696,110 filed on May 6, 1991, which is a continuation-in-part application of our copending application Ser. No. 07/358,536 filed May 26, 1989, which is in turn a continuation application of application Ser. No. 06/813,723 filed Dec. 27, 1985, all now abandoned.

The present invention relates to beta-lactams and their production. More particularly, the invention relates to novel beta-lactam compounds of the formula:

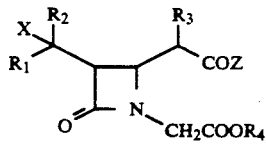

wherein $R_1$ and $R_2$ are, the same or different, each a hydrogen atom or a lower alkyl group, $R_3$ is a hydrogen atom or a lower alkyl group having a beta-configuration, $R_4$ is a carboxyl-protecting group, X is a hydrogen atom or a protected hydroxyl group and COZ is a protected thiolcarboxyl group, and their production and use.

Since the successful isolation of an antibiotic substance "thienamycin" from nature [U.S. Pat. No. 3,950,357; J.Am.Chem.Soc., 100, 313 (1978)], various carbapenem compounds have been reported. Among them, there are known some carbapenem compounds substituted with an alkyl group at the 1-position, and 1-methylcarbapenem compounds are particularly notable in exerting strong antimicrobial activity against various microorganisms with excellent stability in living bodies [EP-0071908A; Heterocycles, 21, 29 (1984)]. However, their synthetic methods as heretofore reported are troublesome by requiring a lengthy series of reaction steps. Further, those methods are defective in that the stereospecific formation of the 1-methyl group is not possible.

As the result of an extensive study, it has now been discovered that the beta-lactam compounds (I) are valuable intermediates for the production of 1-alkylcarbapenem compounds having the following fundamental skeleton:

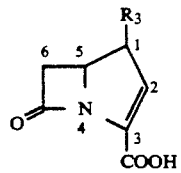

wherein $R_3$ is as defined above, particularly in making it possible to form an alkyl group at the 1-position stereospecifically. This invention is based on the above discovery.

In the present specification, the term "lower" used in connection with an alkyl group is intended to mean the one having not more than 10 carbon atoms, preferably not more than 8 carbon atoms, more preferably not more than 5 carbon atoms. For instance, the lower alkyl group represented by $R_1$, $R_2$ or $R_3$ may be an alkyl group of 1 to 4 carbon atoms such as methyl, ethyl, n-propyl or isopropyl.

The hydroxyl-protecting group (i.e. the group protecting a hydroxyl group) in the protected hydroxyl group may be lower alkoxycarbonyl such as $C_1$-$C_4$ alkoxycarbonyl (e.g. t-butyloxycarbonyl), halogenated lower alkoxycarbonyl such as halogenated ($C_1$-$C_3$)alkoxycarbonyl (e.g. 2-iodoethyloxycarbonyl, 2,2,2-trichloroethyloxycarbonyl), ar(lower)alkoxycarbonyl such as phenyl($C_1$-$C_4$)alkoxycarbonyl optionally bearing any substituent(s) on the benzene ring (e.g. benzyloxycarbonyl, o-nitrobenzyloxycarbonyl, p-nitrobenzyloxycarbonyl, p-methoxybenzyloxycarbonyl), tri(lower)alkylsilyl such as tri($C_1$-$C_4$)alkylsilyl (e.g. trimethylsilyl, t-butyldimethylsilyl), substituted methyl such as $C_1$-$C_4$ alkoxymethyl (e.g. methoxymethyl), $C_1$-$C_4$ alkoxy-($C_1$-$C_4$)alkoxymethyl (e.g. 2-methoxyethoxymethyl), $C_1$-$C_4$ alkylthiomethyl (e.g. methylthiomethyl), tetrahydropyranyl, etc.

The carboxyl-protecting group (i.e. the group protecting a carboxyl group) and the thiolcarboxyl-protecting group (i.e. the group protecting a thiolcarboxyl group) in the protected thiolcarboxyl group may be conventional ones, and their specific examples are lower alkyl such as $C_1$-$C_4$ alkyl (e.g. methyl ethyl, isopropyl, t-butyl), halogenated lower alkyl such as halogenated $C_1$-$C_3$ alkyl (e.g. 2-iodoethyl, 2,2,2-trichloroethyl), lower alkoxymethyl such as $C_1$-$C_4$ alkoxymethyl (e.g. methoxymethyl, ethoxymethyl, isobutoxymethyl), lower aliphatic acyloxymethyl such as $C_1$-$C_5$ alkanoyloxymethyl (e.g. acetoxymethyl, propionyloxymethyl, butyryloxymethyl, pivaloyloxymethyl), lower alkoxycarbonyloxyethyl such as 1-($C_1$-$C_4$ alkoxycarbonyloxy)ethyl (e.g. 1-methoxycarbonyloxyethyl, 1-ethoxycarbonyloxyethyl), optionally substituted lower alkenyl such as $C_3$-$C_{10}$ alkenyl optionally substituted with $C_1$-$C_4$ alkyl or phenyl (e.g. allyl, 2-methylallyl, 3-methylallyl, 3-phenylallyl), optionally substituted monoaryl(lower)alkyl such as phenyl(C )alkyl optionally bearing any substituent(s) chosen from $C_1$-$C_4$ alkoxy, nitro, halogen and the like on the benzene ring (e.g. benzyl, p-methoxybenzyl, 2,4-dimethoxybenzyl, o-nitrobenzyl, p-nitrobenzyl, p-chlorobenzyl), optionally substituted diaryl(lower)alkyl such as diphenyl($C_1$-$C_4$)alkyl optionally bearing any substituent(s) chosen from $C_1$-$C_4$ alkoxy and the like on the benzene ring(s) (e.g. diphenylmethyl, di-p-anisylmethyl), aryl such as phenyl optionally substituted with halogen, nitro, $C_1$-$C_4$ alkoxy or the like (e.g. phenyl, p-chlorophenyl, 2,4,5-trichlorophenyl, p-nitrophenyl, o-nitrophenyl, p-methoxyphenyl), heteroaryl such as pyridyl or pyrimidyl optionally substituted with $C_1$-$C_4$ alkyl (e.g. 2-pyridyl, 3-pyridyl, 4-pyridyl, 2-pyrimidyl, 2-(4,6-dimethyl)pyrimidyl), phthalidyl, etc.

The beta-lactam compounds (I) may be produced, for instance, by any of the processes as set forth below.

Process A

The beta-lactam compound (I) is obtainable by reacting a compound of the formula:

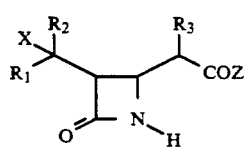

wherein $R_1$, $R_2$, $R_3$, X and COZ are each as defined above with a compound of the formula:

M—CH$_2$COOR$_4$ (III)

wherein R$_4$ is as defined above and M is an activated hydroxyl group in an inert solvent in the presence of a base. Preferred examples of the activated hydroxyl group represented by M are active esters such as sulfonyl esters (e.g. mesylate, tosylate) and halogens (e.g. chlorine, bromine, iodine). If necessary, a phase transfer catalyst may be used.

Examples of the inert solvent are aromatic hydrocarbons (e.g. benzene, toluene), ethers (e.g. tetrahydrofuran, dioxane, diethyl ether), halogenated hydrocarbons (e.g. methylene chloride, dichloroethane, chloroform), ketones (e.g. acetone, methyl isobutyl ketone), acetonitrile, dimethylformamide, dimethylsulfoxide, hexamethylphosphoric amide (HMPT), t-butanol, water, etc. Examples of the base are organic bases (e.g. 1,8-diazabicyclo[5.4.0]undeca-7-ene (DBU), alkali metal hydrides (e.g. sodium hydride, potassium hydride), metal salts of amines (e.g. sodium amide, lithium diisopropylamide, lithium bis(trimethylsilyl)amide), alkali metal hydroxides (e.g. sodium hydroxide, potassium hydroxide), alkali metal carbonates (e.g. sodium carbonate, potassium carbonate), alkali metal alkoxides (e.g. potassium t-butoxide), etc. As the phase transfer catalyst, there may be employed benzyl triethyl ammonium chloride, tetra-n-butyl ammonium bromide, tetraethyl ammonium bromide, etc. The base or the phase transfer catalyst may be used in such an amount that the reaction proceeds smoothly. Occasional heating or cooling is desirable to accelerate or control the reaction.

The compound (II) as the starting material can be produced in the manner as described in U.S. Pat. No. 4,350,631, EP-0054917B or JP-A-82/123182.

Process B

The beta-lactam compound (I) is obtainable by reacting a compound of the formula:

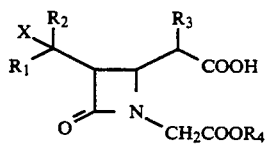

(II')

wherein R$_1$, R$_2$, R$_3$, R$_4$ and X are each as defined above with a thiol compound such as a substituted or unsubstituted thiophenol, 4,6-dimethyl-2-mercaptopyrimidine or 2-mercaptopyridine in the presence of a dehydrating agent (e.g. dicyclohexylcarbodiimide), or by converting said compound (II') into its active ester on the carboxyl group such as acid halide, mixed acid anhydride or acylimidazole derivative and then reacting the resultant active ester with said thiol compound.

The compound (II') as the starting material can be produced by reacting a compound of the formula:

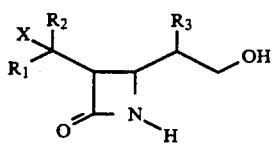

(IV)

wherein R$_1$, R$_2$, R$_3$ and X are each as defined above (produced in the manner as described in EP-0010317B or JP-A-80/89285) with a compound of the formula:

M—CH$_2$COOR$_4$ (III)

wherein R$_4$ and M are each as defined above in an inert solvent in the presence of a base and subjecting the resulting product of the formula:

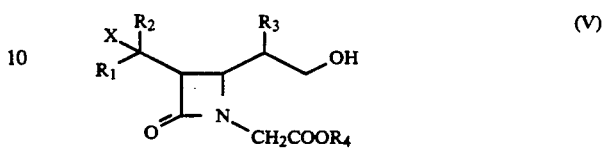

(V)

wherein R$_1$, R$_2$, R$_3$, R$_4$ and X are each as defined above to oxidation.

In the above process, the reaction at the first step may be carried out substantially in the same manner as in Process A. The oxidation at the second step may be effected by a per se conventional procedure for conversion of a primary alcohol into the corresponding carboxylic acid, for instance, by treatment with an oxidizing agent (e.g. chromium (VI) oxide-sulfuric acid, chromium oxide-pyridine).

The beta-lactam compound (I) as produced above can be converted into a carbapenem compound of the formula:

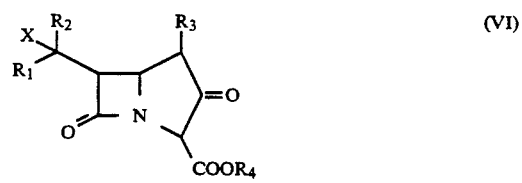

(VI)

wherein R$_1$, R$_2$, R$_3$, R$_4$ and X are each as defined above by treatment with a base in an inert solvent. When, however, R$_3$ represents a lower alkyl group, it is apt to be epimerized on the post-treatment after the reaction, particularly on treatment with a base or concentration. Therefore, special case must be taken to avoid such epimerization.

The thus produced compound (VI) can be converted into the corresponding 1-alkylcarbapenem compound having an antimicrobial activity according to the following route:

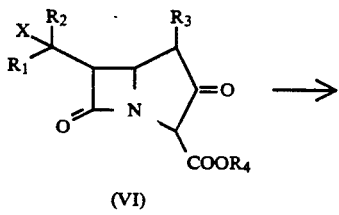

(VI)

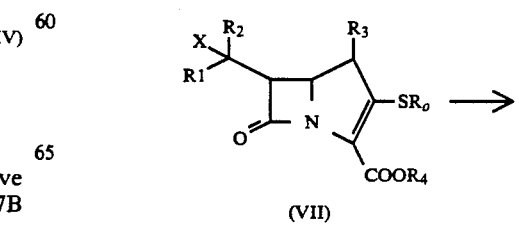

(VII)

-continued

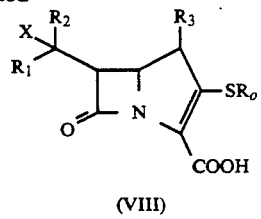

(VIII)

wherein $R_1$, $R_2$, $R_3$, $R_4$ and X are each above and $R_0$ is an organic group.

The compound (VI) is first converted into the carbapenem compound (VII) by the procedure as described in U.S. Pat. No. 4,350,631, European Patent No. 54,917 or Japanese Patent Publication (unexamined) No. 123182/82 or any similar procedure thereto. Then, the resulting carbapenem compound (VII) may be, if necessary, subjected to elimination of the hydroxyl-protecting group and/or elimination of the carboxyl-protecting group to give the carbapenem compound (VIII).

Elimination of the protecting group may be accomplished by a per se conventional procedure, although it is varied with the kind of the protecting group. When, for instance, the hydroxyl-protecting group in the compound (VII) is halogenated lower alkoxycarbonyl or ar(lower) alkoxycarbonyl or the carboxy-protecting group in the compound (VII) is halogenated lower alkyl, ar(lower)alkyl or benzhydryl, it may be eliminated by application of an appropriate reduction. Such reduction may be effected using zinc with acetic acid, tetrahydrofuran or methanol in case of the protecting group being halo(lower)alkoxycarbonyl or halo(lower-)alkyl, or using a catalyst such as platinum or palladium-carbon in case of the protecting group being ar(lower-)alkyloxycarbonyl, ar(lower)alkyl or benzhydryl.

In case of using a catalyst as stated above, the reduction is normally effected in an inert solvent chosen from lower alkanols (e.g. methanol, ethanol), ethers (e.g. tetrahydrofuran, dioxane), organic acids (e.g. acetic acid), water and buffers (e.g. phosphate buffer, morpholinopropanesulfonate buffer), etc. These solvents may be used solely or in combination. The reaction temperature is usually from 0° to 100° C., preferably from 0° to 40° C. The hydrogen pressure may be atmospheric or an elevated one.

Still, such a protecting group as o-nitrobenzyloxycarbonyl or o-nitrobenzyl may be eliminated also by photoreaction.

In the substituent $SR_0$ of the carbapenem compound (VII), $R_0$ may be any one as heretofore used in connection with carbapenem compounds, and its examples include substituted or unsubstituted alkyl or alkenyl having 1 to 10 carbon atoms; cycloalkyl, alkylcycloalkyl or cycloalkylalkyl in which the cycloalkyl group has 3 to 6 carbon atoms; aryl (e.g. phenyl), aralkyl wherein the aryl group is phenyl and the alkyl portion has 1 to 6 carbon atoms; heteroaryl, heteroarylalkyl or heterocycloalkyl, etc. These groups may be optionally bear thereon at least one substituent chosen from amino, mono-, di- or trialkylamino, hydroxyl, alkoxy, mercapto, alkylthio, arylthio (e.g. phenylthio), sulfamoyl, amidino, guanidino, nitro, halo (e.g. chloro, bromo, fluoro), cyano and carboxyl. In the substituents having a hetero ring, the hetero atom(s) in the hetero ring may be chosen from oxygen, nitrogen and sulfur, and their number may range from 1 to 4. The alkyl moiety in the substituents may have 1 to 6 carbon atoms.

In comparison with the above process, carbapenem compounds can be produced much more advantageously according to this invention, which will be hereinafter explained in details.

A typical procedure according to this invention takes the following route:

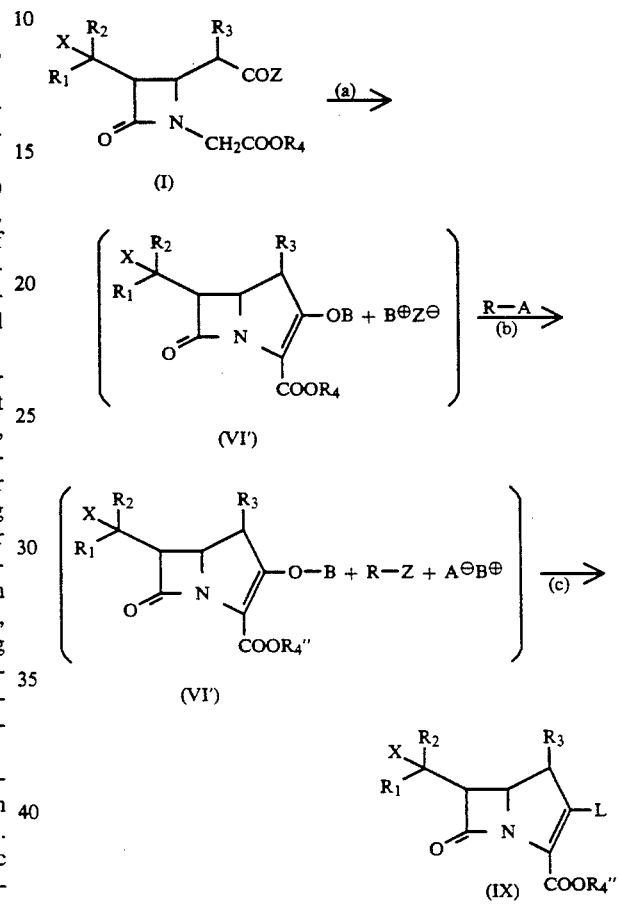

wherein $R_1$, $R_2$, $R_3$, $R_4$, X, Y and Z are each as defined above and L is an activated hydroxyl group such as an active ester of hydroxyl, B is an alkali metal atom and R-A is an alkylating or acylating agent.

For production of the compound (IX) from the compound (I), the latter is first treated with a base in an inert solvent (Step (a)). As the inert solvent, there may be used ethers (e.g. diethyl ether, tetrahydrofuran, dioxane, ethylene glycol dimethyl ether), aromatic hydrocarbons (e.g. benzene, toluene), acetonitrile, dimethylformamide, hexamethylphosphoric triamide (HMPT), t-butanol, etc. Examples of the base are metal salts of amines (e.g. lithium diisopropylamide, lithium bis(trimethylsilyl)amide, sodium amide), metal salts of alcohols (e.g. potassium t-butoxide), alkali metal hydrides (e.g. sodium hydride, potassium hydride), sodium methylsulfinylmethide, etc. The base is to be used in such an amount that the reaction can proceed smoothly, and it may be usually from 1.5 to 3 equivalents to the compound (I). The reaction temperature may be accelerated or controlled by heating or cooling, and it may be normally from −75° to 50° C.

Without isolation of the product, the reaction mixture is then treated with an alkylating or acylating agent (e.g. iodomethane, iodopropane, allyl bromide, benzyl bromide, methyl p-toluene sulfonate) so as to catch the residue of the activating group such as a thiol residue (step (b)), followed by treatment with a hydroxyl-activating agent such as an active esterifying agent for hydroxyl to give the carbapenem compound (IX) (step (c)). The treatment with the alkylating or acylating agent is preferably carried out in the presence of a base in an inert solvent.

As the active ester of hydroxyl represented by the symbol L, there are exemplified substituted or unsubstituted arylsulfonic esters (e.g. benzenesulfonic esters, p-toluenesulfonic esters, p-nitrobenzenesulfonic esters, p-bromobenzenesulfonic esters), lower alkanesulfonic esters (e.g. methanesulfonic esters, ethanesulfonic esters), halo(lower)alkanesulfonic esters (e.g. trifluoromethanesulfonic esters), diarylphosphoric esters (e.g. diphenylphosphoric esters), halides (equal to esters with hydrogen halides) (e.g. chlorides, bromides, iodides), etc. Preferred are p-toluenesulfonic esters, methanesulfonic esters, diphenylphosphoric esters, etc. Accordingly, any reagent which is reacted with the compound (VI') to give the active ester as exemplified above may be used as the active esterifying agent. Examples of the alkali metal atom represented by the symbol B are lithium, sodium, potassium, etc. As the base, there may be used the one as exemplified in step (a) for production of the compound (VI).

When the symbol $R_3$ in the compound (I) is a lower alkyl group, its treatment with a base in an inert solvent affords the enolate (VI'), which retains the steric configuration o the basis of the asymmetric carbon atom at the 5-position of the compound (I). Even after conversion of the enolate (VI') into the compound (IX), the steric configuration of the alkyl group represented by the symbol $R_3$ is unchanged. Thus, adoption of this procedure gives the carbapenem compound (IX) without epimerization. Still, the enolate (VI') in this case has a possibility of taking a chelate structure of the formula:

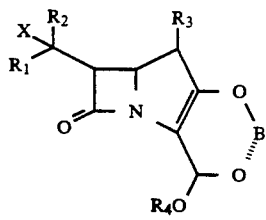

wherein $R_1$, $R_2$, $R_3$, $R_4$, X and B are each as defined above.

The active esterifying agent is to be used in an amount sufficient to effect the reaction smoothly, and its amount may be from 1 to 1.5 equivalents to the compound (I). The reaction temperature may be usually from −78° to 60° C., preferably from −40° to 10° C.

When production of the carbapenem compound (VII) is desired, the above produced compound (IX) may be reacted with a thiol compound of the formula:

$$R_0\text{—SH} \qquad (X)$$

wherein $R_0$ is as defined above. From the industrial viewpoint, it is favorable to subject the reaction mixture comprising the compound (IX) to reaction with the thiol compound without isolation of the compound (IX). In this case, the conversion is representable by the following route:

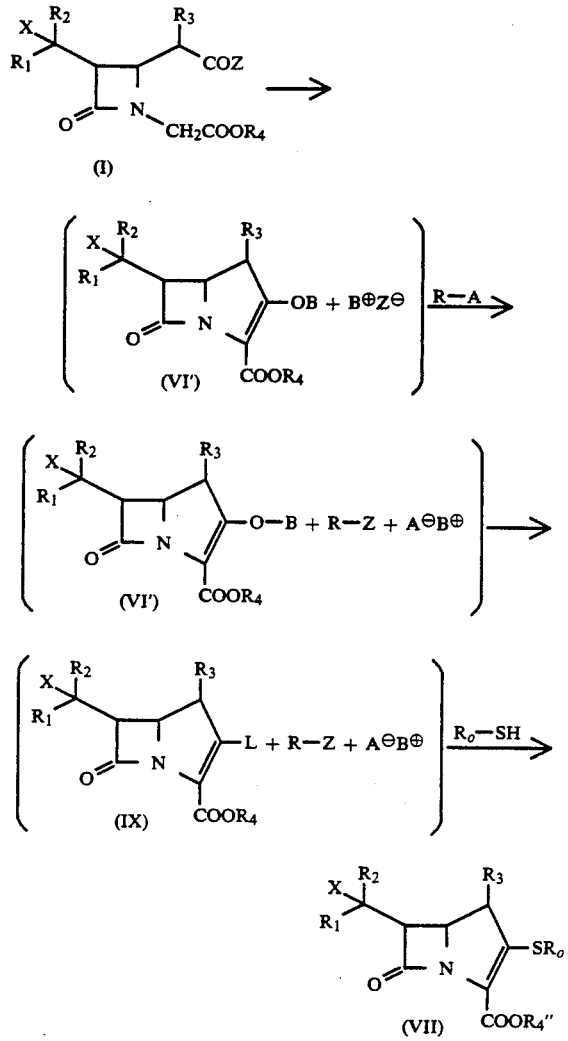

wherein $R_1$, $R_2$, $R_3$, $R_4$, $R_0$, R-A, B, X and Z are each as defined above.

Namely, the compound (I) is converted into the carbapenem compound (IX) in the same manner as previously explained. Without isolation of the compound (IX), the reaction mixture is treated with a mercaptan compound of the formula:

$$R_0\text{—SH} \qquad (X)$$

wherein $R_0$ is as defined above in the presence of a base to give the carbapenem compound (VII). The base to be used in the treatment with the mercaptan compound (X) may be the same as or different from that as used in the cyclization of the compound (I) to the compound (IX). Likewise, the inert solvent to be used in the treatment may be the same as or different from that as used in the cyclization.

As the base, there may be used the one chosen from those as exemplified above. Other examples of the base usuable are organic amines such as triethylamine, diisopropylethylamine, 4-dimethylaminopyridine, 1,8-diazabicyclo-[5.4.0]-7-undecene (DBU), 1,5-diazabicyclo[4.3.0]-5-nonene (DBN) and 1,4-diazabicyclo[2.2.-

2]octane (DABCO). Preferred examples of the solvent which is used for smooth proceeding of the reaction are acetonitrile, dimethylformamide, dimethylsulfoxide, etc.

The base to be used together with the mercaptan compound (X) may be employed in such an amount as can assure the smooth proceeding of the reaction, and its amount may be in a large excess, preferably from 1 to 2 equivalents to the compound (I). The mercaptan compound (X) and the base may be introduced into the reaction system separately. Alternatively, the salts formed between them may be added to the reaction system.

A typical example of the conversion from the beta-lactam compound (I) into the 1-beta-methylcarbapenem compound is shown below.

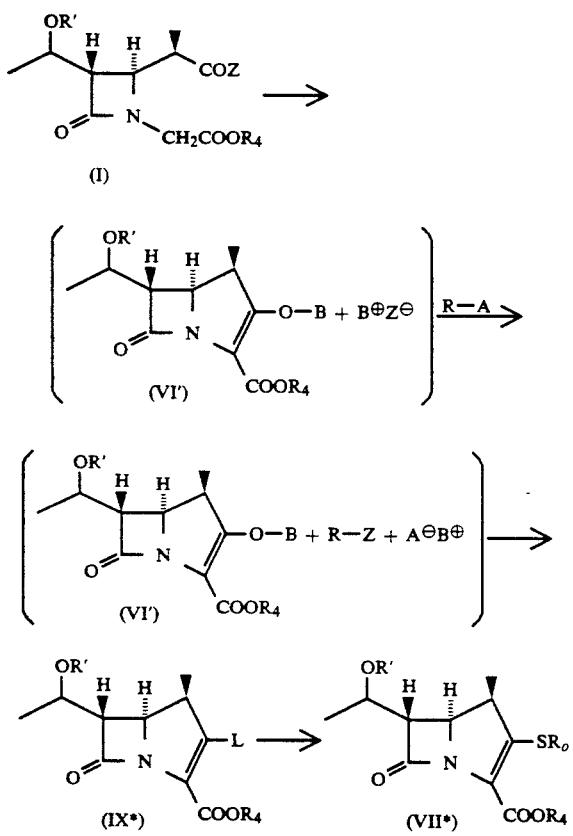

wherein $R_4$, Z, B, R-A, L and $R_0$ are each as defined above and R' is a hydroxyl-protecting group.

Namely, 1) the beta-lactam compound (I) is treated with a base in an inert solvent, 2) the residue $Z^-$ is caught with an alkylating or acylating agent and then 3) the resulting product is treated whit a hydroxyl-activating group such as an active esterifying agent for hydroxyl. When desired, 4) the resultant product is reacted with the mercaptan compound (X) in the presence of a base or the salt of the mercaptan compound (X) with the base. These reactions may be carried out in a single reaction vessel in order to give the carbapenem compound (IX*) or (VII*).

Alternatively, the compound (I) may be subjected to the reaction in 1), followed by post-treatment to give the compound of the formula:

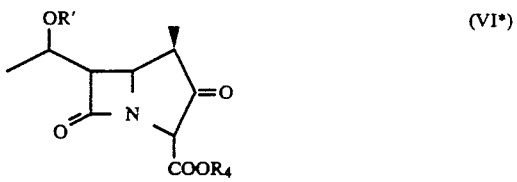

wherein $R_4$ and R' are each as defined above. The beta-methyl group at the 1-position is likely to be epimerized when the product is stored in a high concentration solution or in a polar solvent such as acetonitrile. Thus, the stereospecific production of the compound (IX*) from the compound (VI*) as once isolated in a large scale would have a technical problem. To the contrary, the conversion of not the compound (VI*) but the compound (VI') into the compound (IX*) is advantageous, because the production of the compound (IX*) or (VII*) can be accomplished without epimerization of the methyl group at the 1-beta-position.

In the beta-lactam compound (I), the carbon atoms at the 3- and 4-positions and the carbon atom bonding to the beta-lactam ring and in the substituent attached to the 4-position of such beta-lactam ring are all asymmetric carbon atoms. Further, in the case that all of $R_1$, $R_2$ and X are different one another (e.g. $R_1$=methyl, $R_2$=hydrogen, X=hydroxyl), the carbon atom bonding to the beta-lactam ring and in the substituent attached to the 3-position of such beta-lactam ring is an asymmetric carbon atom. Accordingly, the beta-lactam compound of the formula (I) covers optical isomers and stereo isomers due to the asymmetric carbon atoms. Among those optical isomers and stereo isomers, the compounds of the following formula:

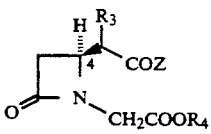

wherein $R_3$, $R_4$ and Z are each as defined above are particularly preferred in having the same configuration as that of naturally occuring thienamycin on the carbon atom at the 4-position.

Practical and presently preferred embodiments of the invention are illustratively shown in the following Examples and References Examples. This invention is, however, not limited to these examples. In these examples, the abbreviations have the following meanings: TBDMS, t-butyldimethylsilyl; Ph, phenyl; tBu, t-butyl; PNB, p-nitrobenzyl; PMB, p-methoxybenzyl; Im, 1-imidazolyl; Bt, 1-benzotriazolyl; Ac, acetyl; PNZ, p-nitrobenzyloxycarbonyl; DAM, di(p-anisyl)methyl; Z, benzyloxycarbonyl; Me, methyl.

EXAMPLE 1-1

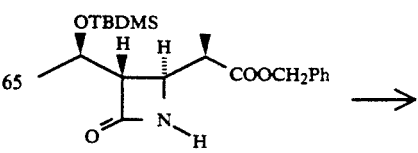

-continued

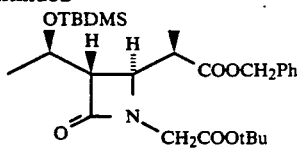

To a solution of (3S,4S)-3-[(1R)-1-t-butyldimethyl-silyloxyethyl]-4-[(1R)-1-benzyloxycarbonylethyl]-azetidin-2-one (755 mg) in methylene chloride (10 ml), there were added successively t-butyl bromoacetate (1.88 g), 50% sodium hydroxide (620 mg) and triethylbenzylammonium chloride (220 mg), followed by stirring at room temperature for 2 hours. The reaction mixture was diluted with water and diethyl ether. The aqueous layer was separated from the organic layer and extracted two times with diethyl ether. The extracts were combined with the organic layer, washed with water two times and brine three times, dried over sodium sulfate and evaporated. The residue was purified by silica gel chromatography to give (3S,4S)-3-[(1R)-1-t-butyldimethyl-silyloxyethyl]-4-[(1R)-1-benzyloxycarbonylethyl]-1-(t-butyloxycarbonylmethyl)azetidin-2-one.

IR $\nu_{max}^{neat}$ (cm$^{-1}$): 1755, 1730, 1450, 1400, 1380, 1360, 1242, 1220, 1150, 830, 765, 740, 685.

NMR δ (CDCl$_3$): 0.04 (3H, s), 0.07 (3H, s), 0.85 (9H, s), 1.23 (3H, d, J =6.3 Hz), 1.24 (3H, d, J =6.9 Hz), 1.44 (9H, s), 2.90 (1H, qd, J =6.9 and 3.6 Hz), 2.99 (1H, dd, J =2.0 and 6.6 Hz), 3.83 (2H, m), 5.10 (2H, s), 7.35 (5H, s).

EXAMPLE 1-2

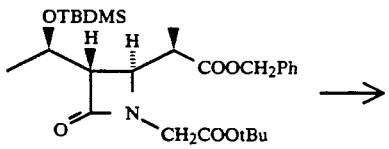

A solution of (3S,4S)-3-[(1R)-1-t-butyldimethyl-silyloxyethyl]-4-[(1R)-1-benzyloxycarbonylethyl]-1-(t-butyloxycarbonylmethyl)azetidin-2-one (0.45 g) in 99.5% ethanol (6 ml) was subjected to hydrogenation at room temperature in the presence of 10% palladium-carbon (90 mg) under atmospheric pressure, followed by filtration to remove the catalyst. The filtrate was evaporated to give (3S,4S)-3-[(1R)-1-t-butyldimethyl-silyloxyethyl]-4-[(1R)-1-carboxylethyl]-1-(t-butyloxycarbonylmethyl)azetidin-2-one.

IR $\nu_{max}^{neat\,(cm-1)}$: 1760, 1740, 1730, 1455, 1360, 1245, 1224, 1150, 830, 770, 745.

NMR δ (CDCl$_3$) 0.06 (3H, s), 0.08 (3H, s), 0.87 (9H, s), 1.24 (3H, d, J =6.3 Hz), 1.25 (3H, d, J =7.3 Hz), 1.48 (9H, s), 2.94 (1H, qd, J =7.1 and 3.0 Hz), 3.04 (1H, dd, J =2.3 and 5.5 Hz), 3.98 (2H, m), 4.00 (1H, m), 4.21 (1H, m).

EXAMPLE 1-3(1)

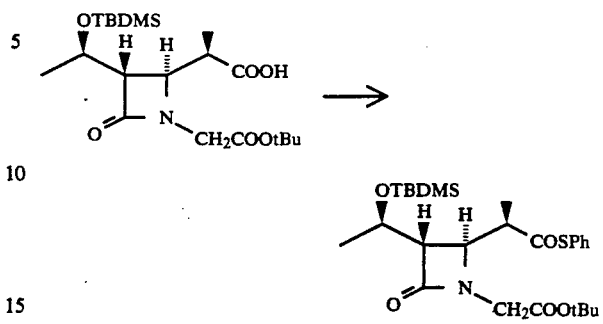

A mixture of (3S,4S)-3-[(1R)-1-t-butyldimethyl-silyloxyethyl]-4-[(1R)-1-carboxylethyl]-1-(t-butyloxycarbonylmethyl)azetidin-2-one (1.29 g) and N,N'-carbonyldiimidazole (604 mg) in dry acetonitrile (25 ml) was stirred at room temperature for 1 hour. To the mixture, there were added successively a solution of thiophenol (410 mg) in dry acetonitrile (6 ml) and a solution of triethylamine (377 mg) in dry acetonitrile (6 ml). After stirring at room temperature for 0.5 hour, the reaction mixture was diluted with ethyl acetate and dilute hydrochloric acid. The aqueous layer was separated from the organic layer and extracted with ethyl acetate three times. The extracts were combined with the organic layer, washed with brine two times, dried over sodium sulfate and evaporated. The residue was purified by silica gel chromatography to give (3S,4S)-3-[(1R)-1-t-butyldimethylsilyloxyethyl]-4-[(1R)-1-phenylthiocarbonylethyl]-1-(t-butyloxycarbonylmethyl)azetidin-2-one.

IR $\nu_{max}^{neat}$ (cm$^{-1}$): 1760, 1740, 1705, 1367, 1250, 1227, 835, 770, 740.

EXAMPLE 1-3(2)

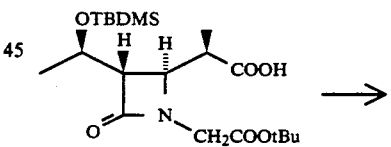

In the same manner as in Example 1-3(1) but replacing thiophenol by p-chlorothiophenol, there was obtained (3S,4S)-3-[(1R)-1-t-butyldimethylsilyloxyethyl]-4-[(1R)-1-p-chlorophenylthiocarbonylethyl]-1-(t-butoxycarbonylmethyl)azetidin-2-one.

IR $\nu_{max}^{neat}$ (cm$^{-1}$): 1760, 1740, 1705, 1480, 1365, 1260, 1230, 1155, 1095, 838, 775.

NMR δ (CDCl$_3$) 0.10 (6H, s), 0.89 (9H, s), 1.26 (3H, d, J =6.3 Hz), 1.31 (3H, d, J =6.9 Hz), 1.43 (9H, s), 3.02 (1H, dd, J =2.3 and 6.9 Hz), 3.14 (1H, qd, J =3.3 and 6.9 Hz), 3.92 (2H, m), 7.34 (4H, m).

EXAMPLE 1-3(3)

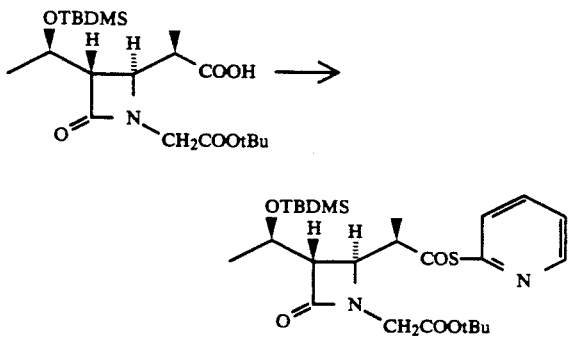

To a solution of (3S,4S)-3-[(1R)-1-t-butyldimethylsilyloxyethyl]-4-[(1R)-1-carboxyethyl]-1-(t-butyloxycarbonylmethyl)azetidin-2-one (100 mg) and 2-mercaptopyridine (35 mg) in dry tetrahydrofuran (4 ml), there was added 1-ethyl-3-(3-dimethylaminopropyl)carbodiimide hydrochloride (100 mg) under ice-cooling, followed by stirring overnight. The reaction mixture was diluted with diethyl ether and water. The organic layer was separated from the aqueous layer, washed with brine, dried over sodium sulfate and distilled off to remove the solvent to give (3S,4S)-3-[(1R)-1-t-butyldimethylsilyloxyethyl]-4-[(1R)-1-(2-pyridylthio)carbonylethyl]-1-(t-butyloxycarbonylmethyl)azetidin-2-one.

IR $\nu_{max}^{neat}$ (cm$^{-1}$): 1755, 1690, 1360, 1247, 1220, 1142, 830, 770.

EXAMPLE 1-4

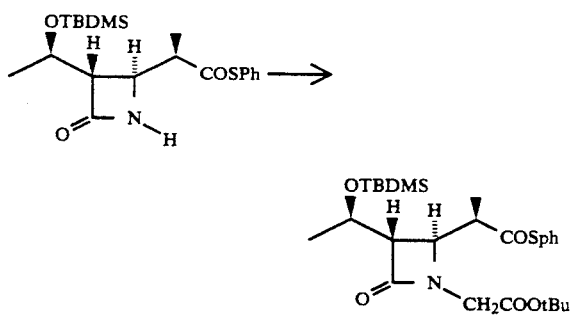

To a suspension of sodium hydride (31 mg) in dry dimethylformamide (4.3 ml), there were added successively t-buty alpha-bromoacetate (835 mg) and (3S,4S)-3-[(1R)-1-t-butyldimethylsilyloxyethyl]-4-[(1R)-1-phenylthiocarbonylethyl]azetidin-2-one (0.42 g), and the resultant mixture was stirred at room temperature for 1 hour under a nitrogen stream. The reaction mixture was diluted with diethyl ether and adjusted to pH 6.86 with a phosphoric acid buffer solution. The aqueous layer was separated from the organic layer and extracted with diethyl ether three times. The extracts were combined with the organic layer, washed three times with brine, dried over sodium sulfate and evaporated. The residue was purified by silica gel chromatography to give (3S,4S)-3-[(1R)-1-t-butyldimethylsilyloxyethyl]-4-[(1R)-1-phenylthiocarbonylethyl]-1-(t-butyloxycarbonylmethyl)azetidin-2-one.

The IR spectrum of the product thus obtained was identical with that of the product in Example 1-3(1).

EXAMPLE 1-5

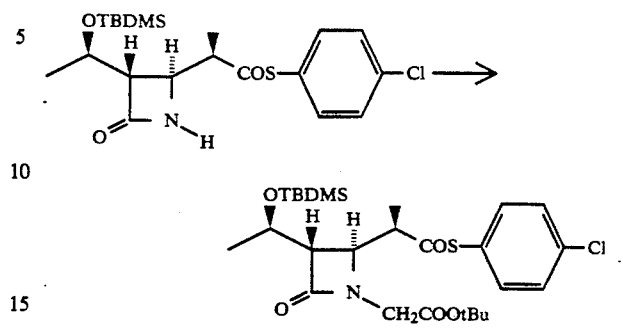

In the same manner as in Example 1-1, there was obtained (3S,4S)-3-[(1R)-1-t-butyldimethylsilyloxyethyl]-4-[(1R)-1-p-chlorophenylthiocarbonylethyl]-1-t-butyloxycarbonylmethylazetidin-2-one from (3S,4S)-3-[(1R)-1-t-butyldimethylsilyloxyethyl]-4-[(1R)-1-p-chlorophenylthiocarbonylethyl]azetidin-2-one.

The IR spectrum and NMR spectrum of the product thus obtained were identical with those of the product in Example 1-3(2).

EXAMPLE 2-1

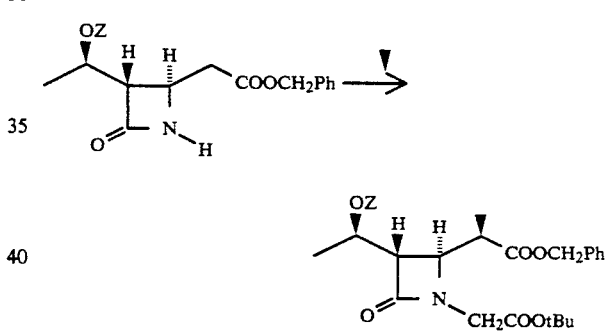

To a solution of (3S,4S)-3-[(1R)-1-t-benzyloxycarbonyloxyethyl]-4-[(1R)-1-benzyloxycarbonylethyl]azetidin-2-one (71.94 g) in dry dimethylformamide (700 ml), there were added successively t-butyl bromoacetate (68.25 g) and sodium hydride (9.24 g, 50% oil suspension) with ice-cooling, followed by stirring for 1 hour. The reaction mixture was diluted with a 10% aqueous ammonium chloride solution (500 ml), stirred for 30 minutes and extracted with toluene (2 liters). The extract was washed with brine, dried over sodium sulfate and evaporated. The residue was purified by silica gel chromatography to give (3S,4S)-3-[(1R)-1-benzyloxycarbonyloxyethyl]-4-[(1R)-1-benzyloxycarbonylethyl]-1-(t-butyloxycarbonylmethyl)azetidin-2-one.

IR $\nu_{max}^{neat}$ (cm$^{-1}$): 1765 (sh), 1740, 1455, 1370, 1268, 1160.

NMR δ (CDCl$_3$) 1.18 (3H, d, J =6.9 Hz), 1.45 (3H, d, J =6.3 Hz), 1.45 (9H, s), 2.86 (1H, m), 3.26 (1H, dd, J =2.0 and 9.0 Hz), 3.55 (1H, d, J =18 Hz), 4.04 (1H, dd, J =2.0 and 4.6 Hz), 4.10 (1H, d, J =18 Hz).

EXAMPLE 2-2

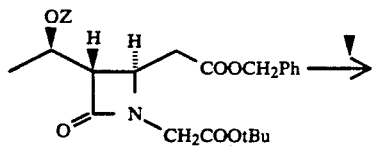

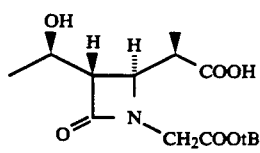

A solution of (3S,4S)-3-[(1R)-1-benzyloxycarbonyloxyethyl]-4-[(1R)-1-benzyloxycarbonylethyl]-1-(t-butyloxycarbonylmethyl)azetidin-2-one (81.50 g) in ethanol (800 ml) was subjected to hydrogenation at room temperature in the presence of 10% palladium-carbon (8.15 g) under atmospheric pressure, followed by filtration to remove the catalyst. The filtrate and the washings were combined and evaporated to give (3S,4S)-3-[(1R)-1-hydroxyethyl]-4-[(1R)-1-carboxyethyl]-1-(t-butyloxycarbonylmethyl)azetidin-2-one.

IR $\nu_{max}^{neat}$ (cm$^{-1}$): 1740, 1720, 1440, 1360.

NMR δ (CDCl$_3$) 1.28 (3H, d, J = 6.9 Hz), 1.33 (3H, d, J = 6.6 Hz), 2.84 (1H, m), 3.09 (1H, dd, J = 2.0 and 6.6 Hz), 3.76 (1H, d, J = 18 Hz), 4.03 (1H, dd, J = 2.0 and 5.3 Hz).

EXAMPLE 2-3

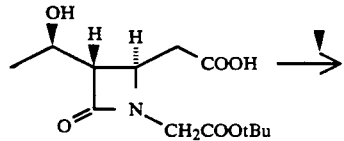

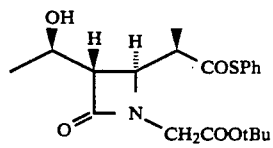

In the same manner as in Example 1-3(1), there was obtained (3S,4S)-3-[(1R)-1-hydroxyethyl]-4-[(1R)-1-phenylthiocarbonyethyl]-1-(t-butyloxycarbonylmethyl)azetidin-2-one from (3S,4S)-3-[(1R)-1-hydroxyethyl]-4-[(1R)-1-carboxyethyl]-1-(t-butyloxycarbonylmethyl)azetidin-2-one.

IR $\nu_{max}^{nujol}$ (cm$^{-1}$): 1745, 1725, 1290, 1230, 1140, 950, 750.

EXAMPLE 3-1

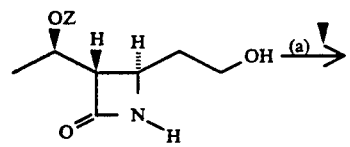

-continued

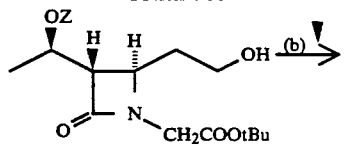

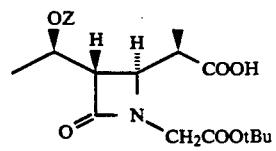

(a) To a solution of (3S,4R)-3-[(1R)-1-benzyloxycarbonyloxyethyl]-4-[(1R)-1-hydroxymethylethyl]-2-azetidinone (30.7 g) in acetone (300 ml), there were added t-butyl bromoacetate (33.0 g) and potassium carbonate (27.6 g), followed by stirring under reflux for 17 hours. The reaction mixture was cooled down to room temperature and filtered to remove insoluble materials. The filtrate contained (3S,4R)-3-[(1R)-1-benzyloxycarbonyloxyethyl]-4-[(1R)-1-hydroxymethylethyl]-1-t-butoxycarbonylmethyl-2-azetidinone.

IR $\nu_{max}^{neat}$ (cm$^{-1}$) 1735, 1360, 1250, 1150, 1030, 955).

(b) The filtrate was diluted with water (15 ml) and treated with the Jones reagent, which was prepared from chromium trioxide (16.92 g), 98% sulfuric acid (26.52 g) and water (49.2 g), while ice-cooling for 1 hour. The reaction mixture was quenched with isopropanol and diluted with ethyl acetate (1 liter) and water (300 ml). The organic layer was washed with brine (300 ml×4), dried over magnesium sulfate (50 g) and evaporated in vacuo to give an oily residue, which was purified by silica gel chromatography to give (3S,4S)-3-[(1R)-1-benzyloxycarbonyloxyethyl]-4-[(1R)-1-carboxyethyl]-1-t-butoxycarbonylmethyl-2-azetidinone (23.73 g, 54.5%).

IR $\nu_{max}^{neat}$ (cm$^{-1}$) 1735, 1450, 1365, 1250, 1150, 1040.

NMR δ (CDCl$_3$) 1.19 (3H, d, J = 6.9 Hz), 1.46 (9H, s), 3.26 (1H, dd, J = 2.3 and 8.6 Hz), 4.06 (1H, dd, J=2.3 and 4.0 Hz), 7.36 (5H, s).

EXAMPLE 3-2

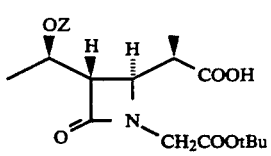

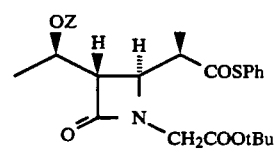

To a solution of (3S,4S)-3-[(1R)-1-benzyloxycarbonyloxyethyl]-4-[(1R)-1-carboxyethyl]-1-t-butoxycarbonylmethyl-2-azetidinone (23.75 g) in dry acetonitrile (237 ml), there was added N,N'-carbonyldiimidazole (10.55 g) under ice-cooling, followed by stirring for 0.5 hour. Thiophenol (7.21 g) and triethylamine (6.62 g) were then added thereto under ice-cooling, followed by stirring for 2.5 hours. The reaction mixture was diluted with ethyl acetate (500 ml) and washed with 1N hydrochloric acid (200 ml). The aqueous layer was separated from the organic layer and extracted with ethyl acetate (200 ml×2). The extract was combined with the organic layer, washed with brine (300 ml×3), dried over magnesium sulfate and evaporated in vacuo to give an oily residue, which was purified by silica gel chromatography to obtain (3S,4S)-3-[(1R)-1-benzyloxycarbonyloxyethyl]-4-[(1R)-1-phenylthiocarbonylethyl]-1-t-butoxycarbonylmethyl-2-azetidinone (19.46 g, 67.64%).

IR $v_{max}^{neat}$ (cm$^{-1}$): 1760, 1735, 1700, 1440, 1365, 1255, 1150, 1045, 950, 740.

NMR δ (CDCl$_3$) 1.25 (3H, d, J =6.9 Hz), 1.44 (9H, s), 1.47 (3H, d, J =6.2 Hz), 3.12 (1H, m), 4.13 (1H, dd, J =2.6 and 4.5 Hz), 7.36 (10H, m).

EXAMPLE 4-1

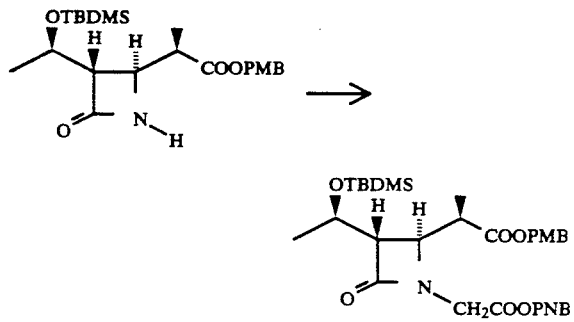

To a solution of (3S,4S)-3-[(1R)-1-t-butyldimethylsilyloxyethyl]-4-[(1R)-1-p-methoxybenzyloxycarbonylethyl]azetidin-2-one (1.12 g) in methylene chloride (14 ml), there were successively added p-nitrobenzyl alpha-bromoacetate (1.09 g), 50 % aqueous sodium hydroxide solution (0.85 g) and triethylbenzylammonium chloride (303 mg), followed by stirring at room temperature for 30 minutes. The reaction mixture was diluted with water and extracted with a mixture of diethyl ether and methylene chloride (3:1) three times. The organic layer was washed successively with water two times and brine three times, dried over sodium sulfate and evaporated. The residue was purified by silica gel chromatography to give (3S,4S)-3-[(1R)-1-t-butyldimethylsilyloxyethyl]-4-[(1R)-1-p-methoxybenzyloxycarbonylethyl]-1-(p-nitrobenzyloxycarbonylmethyl)azetidin-2-one.

IR $v_{max}^{neat}$ (cm$^{-1}$): 1760, 1742, 1607, 1515, 1458, 1342, 1241, 1170, 830, 747.

NMR δ (CDCl$_3$) 0.01 (3H, s), 0.05 (3H, s), 0.83 (9H, s), 2.86 (1H, qd, J=7.2 and 3.0 Hz), 3.00 (1H, dd, J=2.3 and 6.6 Hz), 3.80 (3H, s), 5.01 (2H, m), 5.20 (2H, s), 6.88 (2H, d, J=8.6 Hz), 7.49 (2H, d, J=8.9 Hz), 8.22 (2H, d, J=8.6 Hz).

EXAMPLE 4-2

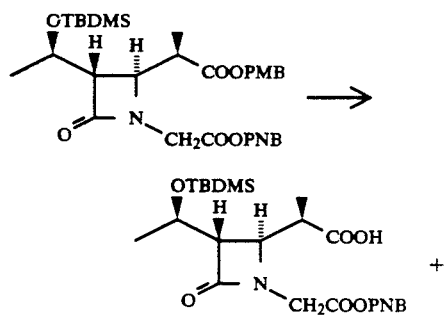

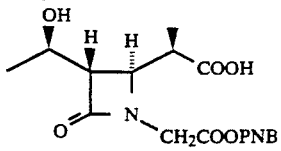

To a solution of (3S,4S)-3-[(1R)-1-t-butyldimethylsilyloxyethyl]-4-[(1R)-1-p-methoxybenzyloxycarbonylethyl]-1-(p-nitrobenzyloxycarbonylmethyl)azetidin-2-one (142 mg) in dry methylene chloride, there was BF$_3$—Et$_2$O complex (163 mg) under ice-cooling, followed by stirring at room temperature. The reaction mixture was poured into a cold aqueous sodium bicarbonate solution, acidified with dilute hydrochloric acid and extracted with ethyl acetate three times. The organic layer was washed successively with dilute hydrochloric acid and brine, dried over sodium sulfate and evaporated., The residue was purified by silica gel chromatography to give (3S,4S)-3-[(1R)-1-t-butyldimethylsilyloxyethyl]-4-[(1R)-1-carboxyethyl]-1-(p-nitrobenzyloxycarbonylmethyl)azetidin-2-one (Compound A) and (3S,4S)-3-[(1R)-1-hydroxyethyl]-4-[(1R)-1-carboxyethyl]-1-(p-nitrobenzyloxycarbonylmethyl)azetidin-2-one (Compound B).

Compound A

IR $v_{max}^{neat}$ (cm$^{-1}$): 3100 (broad), 1760, 1730, 1520, 1342, 1245, 1180, 830, 770.

NMR δ (CDCl$_3$) 0.03 (3H, s), 0.07 (3H, s), 0.85 (9H, s), 1.25 (3H, d, J=6.3 Hz), 1.26 (3H, d, J=7.3 Hz), 2.91 (1H, qd, J=3.0 and 7.3 Hz), 3.05 (1H, dd, J=2.3 and 5.9 Hz), 4.13 (2H, m), 5.26 (2H, s), 7.52 (2H, d, J=8.9 Hz), 8.23 (2H, d, J=8.9 Hz).

Compound B

IR $v_{max}^{neat}$ (cm$^{-1}$): 3430 (broad), 1760, 1735, 1705, 1520, 1345, 1180, 745.

EXAMPLE 5-1

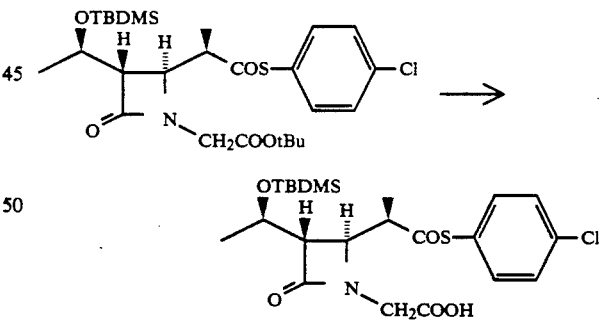

To a solution of (3S,4S)-3-[(1R)-1-t-butyldimethylsilyloxyethyl]-4-[(1R)-1-p-chlorophenylthiocarbonylethyl]-1-(t-butyloxycarbonylmethyl)azetidin-2-one (200 mg) in dry methylene chloride (1.5 ml), there was added BF$_3$—ET$_2$O complex (263 mg), followed by stirring at room temperature for 1 hour. After evaporation of the solvent, the residue was dissolved in methanol (0.5 ml), diluted with brine and extracted with ethyl acetate. The organic layer was washed with brine, dried over sodium sulfate and evaporated to give (3S,4S)-3-[(1R)-1-hydroxyethyl]-4-[(1R)-1-p-chlorophenylthiocarbonylethyl]-1-(carboxymethyl)azetidin-2-one as a crude product. The crude product, t-butyldimethylsilyl chloride (246 mg) and imidazole (151 mg) were dissolved in dry dimethylformamide (2.5 ml) and allowed to stand at room temperature overnight. The reaction mixture was poured into cold brine, adjusted with 1M potassium hydrogensulfate to pH and extracted with diethyl ether three times. The organic layer was washed with brine two times, dried over sodium sulfate and evaporated. The residue was purified by silica gel chromatography to give (3S,4S)-3-[(1R)-1-t-butyldimethylsilyloxyethyl]-4-[(1R)-1-p-chlorophenylthiocarbonylethyl]-1-(carboxymethyl)azetidin-2-one.

IR $\nu_{max}^{neat}$ (cm$^{-1}$): 3300 (broad), 1760, 1740, 1700, 1480, 1382, 1250, 1140, 1087, 830, 775.

EXAMPLE 5-2

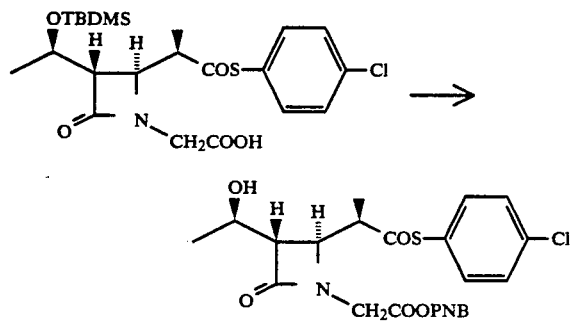

To a mixture of (3S,4S)-3-[(1R)-1-t-butyldimethylsilyloxyethyl)-4-[(1R)-1-p-chlorophenylthiocarbonylethyl]-1-carboxymethylazetidin-2-one (70 mg) and p-nitrobenzyl alcohol (24 ml) in ethyl acetate (0.3 ml), there was added a solution of N,N'-dicyclohexylcarbodiimide (30 mg) in dry ethyl acetate (0.2 ml), and the resultant mixture was stirred at 5° to 10° C. overnight. The precipitated N,N'-dicyclohexylurea was collected by filtration and washed with ethyl acetate. The washing was combined with the filtrate, washed with water and brine, dried over sodium sulfate and distilled off to remove the solvent. The residue was purified by silica gel chromatography to give (3S,4S)-3-[(1R)-1-t-butyl-dimethylsilyloxyethyl)-4-[(1R)-1-p-chlorophenylthiocarbonylethyl]- 1-(1-nitrobenzyloxycarbonylmethyl-)azetidin-2-one.

IR $\nu_{max}^{neat}$ (cm$^{-1}$): 1760, 1750, 1700, 1602, 1520, 1478, 1343, 1250, 1180, 1090, 835, 775, 742.

NMR δ (CDCl$_3$) 0.07 (3H, s), 0.08 (3H, s), 0.88 (9H, s), 1.27 (3H, d, J=6.3 Hz), 1.31 (3H, d, J=7.3 Hz), 3.01 (1H, dd, J=2.6 and 7.1 Hz), 3.14 (1H, qd, J=2.6 and 7.3 Hz), 4.12 (2H, m), 4.17 (2H, m), 5.20 (2H, m), 7.34 (4H, 7.44 (2H, d, J=8.6 Hz), 8.17 (2H, d, J=8.9 Hz).

EXAMPLE 6-1

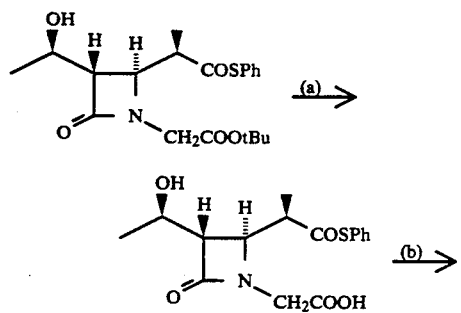

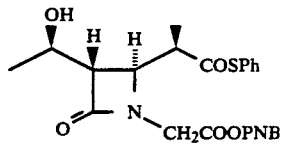

(a) (3S,4S)-3-[(1R)-1-Hydroxyethyl]-4-[(1R)-1-phenylthiocarbonylethyl]-1-(t-butyloxycarbonylmethyl)azetidin-2-one (72.0 g) was dissolved in trifluoroacetic acid (500 ml) under ice-cooling, followed by stirring for 2 hours. The reaction mixture was evaporated in vacuo below 50° C. The residue was then dissolved in toluene (250 ml) and evaporated off to remove the solvent.

(b) To a solution of the residue in dry acetonitrile (720 ml), there were added triethylamine (43.25 g) and p-nitrobenzyl bromide (92.33 g), followed by stirring at room temperature for 1 hour. The reaction mixture was diluted with ethyl acetate (1.5 liters), washed with a 20% aqueous sodium chloride solution several times, dried over sodium sulfate and evaporated. The residue was purified by silica gel chromatography to give (3S,4S)-3-[(1R)-1-hydroxyethyl]-4-[(1R)-1-phenylthiocarbonyethyl]-1-(p-nitrobenzyloxycarbonylmethyl-)azetidin-2-one.

IR $\nu_{max}^{CHCl_3}$ (cm$^{-1}$): 1740, 1680, 1600, 1515, 1360, 250, 1180, 950, 740.

EXAMPLE 6-2

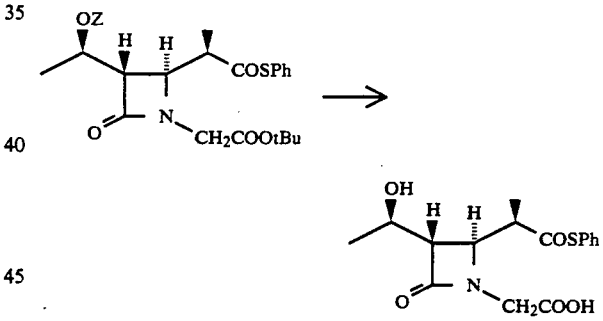

To a solution of (3S,4S)-3-[(1R)-1-benzyloxycarbonyloxyethyl]-4-[(1R)-1-phenylthiocarbonylethyl]-1-t-butoxycarbonylmethylazetidin-2-one (8.5 g) in 1,2-dichloroethane (185 ml), there was dropwise added a solution of boron tribromide (26.4 g) in 1,2-dichloroethane (100 ml) at −10° C. for 20 minutes, followed by stirring at the same temperature for 1 hour. Sodium bicarbonate (40 g) and ice-water (600 g) were added thereto while stirring, and the resultant mixture was diluted with ethyl acetate (200 ml). The aqueous layer was acidified with 2N hydrochloric acid (200 ml), extracted with ethyl acetate and combined with the organic layer. The combined organic layer was washed with brine (200 ml×3), dried over magnesium sulfate and evaporated in vacuo to give (3S,4S)-3-[(1R)-1-hydroxyethyl]-4-[(1R)-1-phenylthiocarbonylethyl]-1-carboxymethylazetidin-2-one (10.4 g, 87.9%.).

IR $\nu_{max}^{Nujol}$ (cm$^{-1}$): 1740, 1710, 1690, 1210, 1130, 1070, 940, 740.

EXAMPLE 6-3

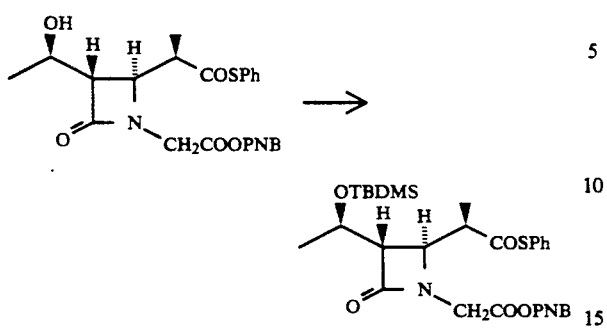

To a solution of (3S,4S)-3-[(1R)-hydroxyethyl]-4-[(1R)-1-phenylthiocarbonylethyl]-1-(p-nitrobenzyloxycarbonylmethyl]azetidin-2-one (52.36 g) in dry dimethylformamide (262 ml), there were added imidazole (16.6 g) and t-butyldimethylchlorosilane (23.38 g), followed by stirring at room temperature for 5 hours. The reaction mixture was diluted with ethyl acetate (1 liter), washed with a 20% aqueous sodium chloride solution. The aqueous layer was separated from the organic layer and extracted with ethyl acetate (500 ml). The extract was combined with the organic layer, washed with a 20% aqueous sodium chloride solution two times, dried over sodium sulfate and evaporated. The residue was purified by silica gel chromatography to give (3S,4S)-3-[(1R)-1-t-butyldimethylsilyloxyethyl]-4-[(1R)-1-phenylthiocarbonylethyl]-1-(p-nitrobenzyloxycarbonylmethyl]azetidin-2-one.

IR $\nu_{max}^{neat}$ (cm$^{-1}$): 1755, 1690, 1600, 1515, 1340, 1250, 1180, 835.

NMR δ (CDCl$_3$) 0.08 (3H, s), 0.09 (3H, s), 0.89 (9H, s), 1.28 (3H, d, J=6.0 Hz), 1.32 (3H, d, J=7.3 Hz), 3.01 (1H, dd, J=2.3 and 7.3 Hz), 3.16 (1H, dd, J=2.3 and 7.3 Hz), 3.96 (1H, d, J=17.8 Hz), 4.17 (2H, m), 4.31 (1H, d, J=17.8 Hz), 5.20 (2H, ABq, J=13.5 Hz), 7.25–7.45 (5H), 8.12 (2H, d, J=8.9 Hz).

EXAMPLE 6-4

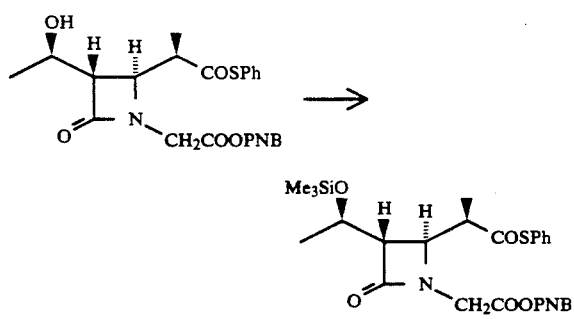

In the same manner as in Example 6-3, there was obtained (3S,4S)-3-[(1R)-1-trimethylsilyloxyethyl]-4-[(1R)-1-phenylthiocarbonylethyl]-1-(p-nitrobenzyloxycarbonylmethyl]azetidin-2-one from (3S,4S)-3-[(1R)-1-hydroxyethyl]-4-[(1R)-1-phenylthiocarbonylethyl]-1-(p-nitrobenzyloxycarbonylmethyl]azetidin-2-one.

IR $\nu_{max}^{neat}$ (cm$^{-1}$): 1760, 1695, 1600, 1520, 1440, 1340, 1250, 1180, 950, 840, 740.

NMR δ (CDCl$_3$): 0.13 (9H, s), 3.04 (1H, dd, J=2.3 and 7.6 Hz), 3.15 (1H, dq, J=2.3 and 7.0 Hz), 3.92 (1H, d, J=18.1 Hz), 4.38 (1H, d, J=18.1 Hz), 5.21 (2H, ABq, J=13.5 Hz), 8.12 (2H, d, J=8.9 Hz).

REFERENCE EXAMPLE 1-1

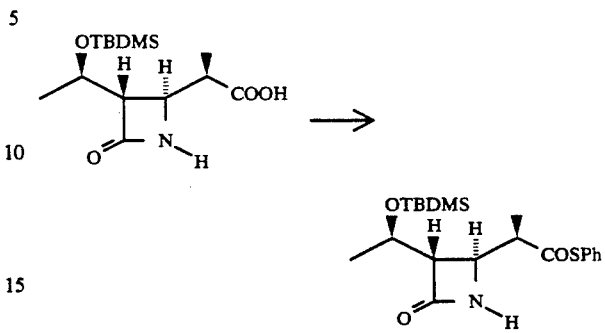

A mixture of (3S,4S)-3-[(1R)-1-t-butyldimethylsilyloxyethyl]-4-[(1R)-1-carboxylethyl]azetidin-2-one (301 mg) and N,N'-carbonyldiimidazole (194 mg) in dry acetonitrile (8.6 ml) was stirred at room temperature for 1 hour. To the reaction mixture, there were successively added thiophenol (132 mg) in dry acetonitrile (2 ml) and triethylamine (121 mg) in dry acetonitrile (2 ml), followed by stirring at room temperature for 30 minutes. The resulting mixture was diluted with ethyl acetate and washed with brine. The aqueous layer was separated from the organic layer and extracted with ethyl acetate two times. The extracts were combined with the organic layer, washed with brine, dried over sodium sulfate and distilled off to remove the solvent. The residue was purified by silica gel chromatography to give (3S,4S)-3-[(1R)-1-t-butyldimethylsilyloxyethyl]-4-[(1R)-phenylthiocarbonylethyl]azetidin-2-one.

IR $\nu_{max}^{neat}$ (cm$^{-1}$): 3200 (broad), 1760, 1700, 1370, 1250, 1140, 955, 830, 773, 740, 680.

REFERENCE EXAMPLE 1-2

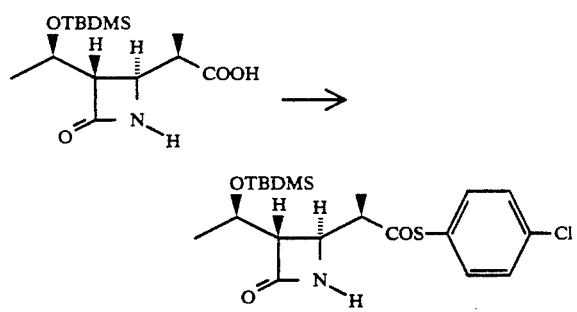

A mixture of (3S,4S)-3-[(1R)-1-t-butyldimethylsilyloxyethyl]-4-[(1R)-1-carboxylethyl]azetidin-2-one (400 mg) and N,N'-carbonyldiimidazole (259 mg) in dry acetonitrile (11 ml) was stirred at room temperature for 1 hour. To the resulting mixture, there were successively added p-chlorothiophenol (231 mg) in dry acetonitrile (3.2 ml) and triethylamine (162 mg) in dry acetonitrile (2.3 ml), followed by stirring at room temperature for 30 minutes. The reaction mixture was diluted with ethyl acetate and washed with brine. The aqueous layer was separated from the organic layer and extracted with ethyl acetate two times. The extracts were combined with the organic layer, washed with dilute hydrochloric acid, brine, aqueous sodium bicarbonate solution and brine, dried over sodium sulfate and distilled off to remove the solvent. The residue was purified by silica gel chromatography to give (3S,4S)-3-[(1R)-1-t-butyldimethylsilyloxyethyl]-4-[(1R)-1-p-chlorophenylthiocarbonylethyl]azetidin-2-one.

IR $\nu_{max}^{neat}$ (cm$^{-1}$): 3250 (broad), 1770, 1750, 1700, 1478, 1247, 1140, 1090, 820, 770.

NMR δ (CDCl$_3$) 0.07 (6H, s), 0.88 (9H, s), 1.18 (3H, d, J=6.3 Hz), 1.33 (3H, d, J=6.9 Hz), 2.97 (1H, m), 3.02 (1H, m), 3.93 (1H, dd, J=2.0 and 5.3 Hz), 4.22 (1H, m), 5.86 (1H, broad, s), 7.36 (4H, m).

REFERENCE EXAMPLE 1-3

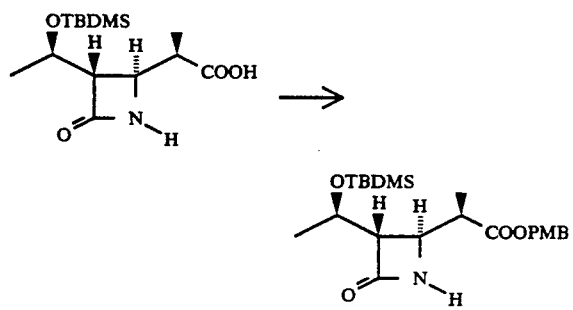

A mixture of (3S,4S)-3-[(1R)-1-t-butyldimethylsilyloxyethyl]-4-[(1R)-1-carboxylethyl]azetidin-2-one (1.00 g), triethylamine (369 mg) and p-methoxybenzyl chloride (779 mg) in dry dimethylformamide (1 ml) was stirred at 70° C. for 2 hours and 40 minutes. The reaction mixture was poured into ice-water, acidified with dilute hydrochloric acid to pH 2 to 3 and extracted with diethyl ether three times. The organic layer was washed with cold 1N aqueous sodium hydroxide solution, water and brine in this order, dried over sodium sulfate and distilled off to remove the solvent. The residue was purified by silica gel chromatography to give (3S,4S)-3-[(1R)-1-t-butyldimethylsilyloxyethyl]-4-[(1R)-1-p-methoxybenzyloxycarbonylethyl]azetidin-2-one.

IR $\nu_{max}^{neat}$ (cm$^{-1}$): 3225 (broad), 1760, 1740, 1605, 1505, 1458, 1240, 1160, 1030, 950, 825, 767.

NMR δ (CDCl$_3$) 0.05 (6H, s), 0.86 (9H, s), 1.13 (3H, d, J=6 Hz), 1.21 (3H, d, J=7 Hz), 2.70 (1H, m), 2.95 (1H, dd, J=2 and 4 Hz), 3.81 (3H, s), 3.89 (1H, dd, J=2 and 5 Hz), 4.16 (1H, m), 5.05 (2H, s), 5.96 (1H, broad, s), 6.87 (2H, d, J=9 Hz), 7.27 (2H, d, J=9 Hz).

REFERENCE EXAMPLE 2-1

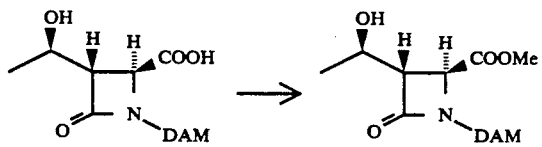

To a solution of (3S,4S)-4-carboxy-3-(1-(R)-hydroxyethyl)-1-di(p-anisyl)methyl-2-azetidinone (34 g) in methanol (310 ml), there was added 98% sulfuric acid (2.9 g). The resultant mixture was heated at 65° C. for 3 hours, cooled down to 40° C., neutralized with 8% aqueous sodium hydroxide solution (15 ml) and concentrated to make a one third volume. The concentrate was diluted with 1,2-dichloroethane (105 ml) and washed with water. The aqueous layer was separated from the organic layer and extracted with 1,2-dichloroethane (105 ml). The extract was combined with the organic layer, washed with water and dried over anhydrous sodium sulfate. After filtration, the filtrate was concentrated in vacuo to give (3S,4S)-4-methoxycarbonyl-3-(1-(R)-hydroxyethyl)-1-di(p-anisyl)methyl-2-azetidinone. m.p., 102°-104° C.

REFERENCE EXAMPLE 2-2

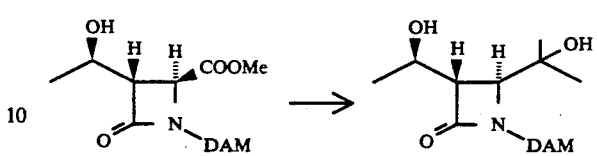

To a solution of (3S,4S)-4-methoxycarbonyl-3-(1-(R)-hydroxyethyl)-1-di(p-anisyl)methyl-2-azetidinone (32.5 g) in dry tetrahydrofuran (310 ml), there was added dropwise a 1M suspension of methyl magnesium bromide in tetrahydrofuran (370 g) at 0°-5° C., and the suspension was stirred at the same temperature as above for 1 hour. 20% Hydrochloric acid (350 ml) was poured into the suspension at 20°-25° C., and the resultant mixture was stirred for 1 hour, followed by extraction with ethyl acetate (110 ml). The aqueous layer was reextracted with ethyl acetate (110 ml). The extracts were combined together, washed successively with brine, a saturated sodium bicarbonate solution and water and dried over anhydrous sodium sulfate. After filtration, the filtrate was concentrated in vacuo to give (3S,4S)-4-(1-hydroxy-1-methylethyl)-3-(1-(R)-hydroxyethyl)-1-di(p-anisyl)methyl-2-azetidinone. m.p., 154°-156° C.

REFERENCE EXAMPLE 2-3

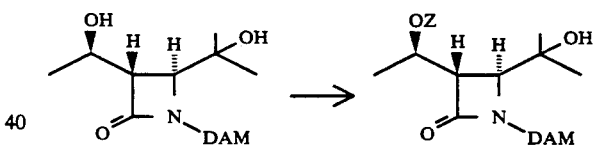

(3S,4S)-4-(1-Hydroxy-1-methylethyl)-3-(1-(R)-hydroxyethyl)-1-di(p-anisyl)methyl-2-azetidinone (26 g) and 4-dimethylaminopyridine (16 g) were dissolved in dry dichloromethane (200 ml). Benzyl chloroformate (20 g) was added dropwise thereto over a period of 1 hour with ice-cooling, and the resultant mixture was stirred for 2 hours and warmed to room temperature, followed by stirring at the same temperature as above for 10 hours. 5% Hydrochloric acid (100 ml) was poured into the reaction mixture with ice-cooling, and the resulting mixture was stirred for 0.5 hour and allowed to stand. The organic layer was washed successively with water, a saturated sodium bicarbonate solution and brine and dried over anhydrous sodium sulfate. After filtration, the filtrate was concentrated in vacuo to give (3S,4S)-4-(1-hydroxyl-methylethyl)-3-(1-(R)-benzyloxycarbonyloxyethyl)-1-di(p-anisyl)methyl-2-azetidinone.

IR $\nu_{max}^{neat}$ (cm$^{-1}$): 3450, 1750, 1615, 1515, 1250, 1180, 1030.

NMR δ (CDCl$_3$) 1.13 (6H, s), 1.38 (3H, d, J=6 Hz), 3.70 (3H, s), 3.75 (3H, s), 5.10 (2H, s), 5.55 (1H, bs), 7.29 (5H, s).

REFERENCE EXAMPLE 2-4

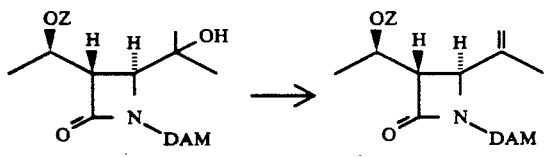

A solution of (3S,4S)-4-(1-hydroxy-1-methylethyl)-3-(1-(R)-benzyloxycarbonyloxyethyl)-1-di(p-anisyl)methyl-2-azetidinone (30 g) in dry toluene (350 ml) was treated with thionyl chloride (9.0 g) at 20°–30° C. for 5 hours in the presence of pyridine (10 ml). Water (100 ml) was added to quench the reaction at 10°–25° C. The organic layer was separated, washed with water and dried over anhydrous sodium sulfate. After filtration, the filtrate was concentrated in vacuo to give an oily residue, which was crystallized from a mixture of cyclohexane and ethyl acetate yield (3S,4S)-4-(1-methylethenyl)-3-(1-(R)-benzyloxycarbonyloxyethyl)-1-di(p-anisyl)methyl-2-azetidinone. m.p., 117°–118° C.

REFERENCE EXAMPLE 2-5

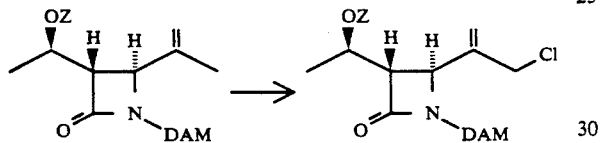

(3S,4S)-4-(1-Methylethenyl)-3-(1-(R)-benzyloxycarbonyloxyethyl)-1-di(p-anisyl)methyl-2-azetidinone (200 g) was dissolved in ethyl acetate (3 liters), and a solution of chlorine in carbon tetrachloride (3.85%, 870 g) was added dropwise thereto at room temperature over a period of 15 minutes, followed by stirring for 1 hour. Water (1 liter) and then 10% aqueous sodium thiosulfate solution (50 ml) were poured into the reaction mixture, which was stirred for 0.5 hour and allowed to stand. The organic layer was washed successively with a saturated sodium bicarbonate solution and brine and dried over anhydrous sodium sulfate. After filtration, the filtrate was concentrated in vacuo to give (3S,4S)-4-(1-chloromethylethenyl)-3-(1-(R)-benzyloxycarbonyloxyethyl)-1-di(p-anisyl)methyl-2-azetidinone. m.p., 84°–85° C.

REFERENCE EXAMPLE 2-6

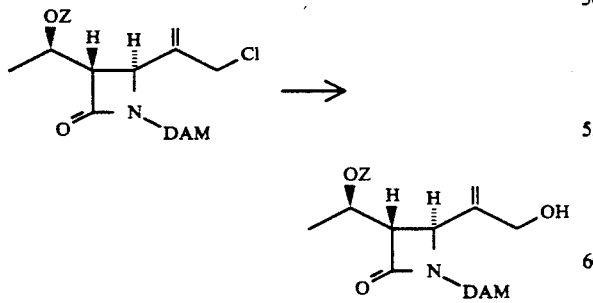

To a solution of (3S,4S)-4-(1-chloromethylethenyl)-3-(1-(R)-benzyloxycarbonyloxyethyl)-1-di(p-anisyl)methyl-2-azetidinone (20 g) in dimethylsulfoxide (160 ml), there were successively added water (40 ml), cuprous oxide (6.76 g) and p-toluenesulfonic acid (7.6 g), and the resultant mixture was warmed to 50 to 55° C. and stirred for 2 hours at the same temperature. After cooling down to room temperature, 1% aqueous phosphoric acid (90 ml) and ethyl acetate (200 ml) were poured into the reaction mixture, followed by stirring for 0.5 hour. An insoluble material was removed by filtration over celite and washed 3 times with ethyl acetate (20 ml). The filtrate and the washings were combined together, and the aqueous layer was separated from the organic layer and extracted with ethyl acetate (200 ml). The organic layer and the extract were combined together, washed with brine and dried over anhydrous sodium sulfate. After filtration, the filtrate was concentrated in vacuo, and the concentrate was crystallized from a mixture of toluene and n-hexane (1 : 1) to give crystals of (3S,4S)-4-(1-hydroxymethylethenyl)-3-(1-(R)-benzyloxycarbonyloxyethyl)-1-di(p-anisyl)methyl-2-azetidinone. m.p., 118°–120° C.

REFERENCE EXAMPLE 2-7

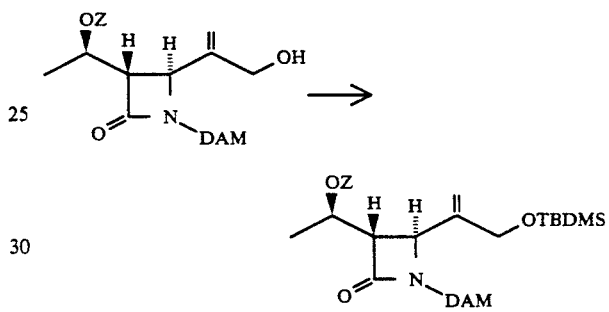

A solution of (3S,4S)-4-(1-hydroxymethylethenyl)-3-(1-(R)-benzyloxycarbonyloxyethyl)-1-di(p-anisyl)methyl-2-azetidinone (20 g) and imidazole (5.6 g) in dry dimethylformamide (45 ml) was treated with t-butyldimethylchlorosilane (6.77 g) at room temperature for 2 hours. The reaction mixture was diluted with cold water (200 ml) and ethyl acetate (150 ml). The aqueous layer was extracted with ethyl acetate (150 ml). The combined extracts were washed successively with 5% hydrochloric acid solution (80 ml×2) and brine (80 ml), and dried over anhydrous sodium sulfate. After filtration, the filtrate was concentrated in vacuo, and the concentrate was crystallized from isopropanol to give crystals of (3S,4S)-4-(1-t-butyldimethylsilyloxymethylethenyl)-3-(1-(R)-benzyloxycarbonyloxyethyl)-1-di(p-anisyl)methyl-2-azetidinone. m.p., 90°–92° C.

REFERENCE EXAMPLE 2-8

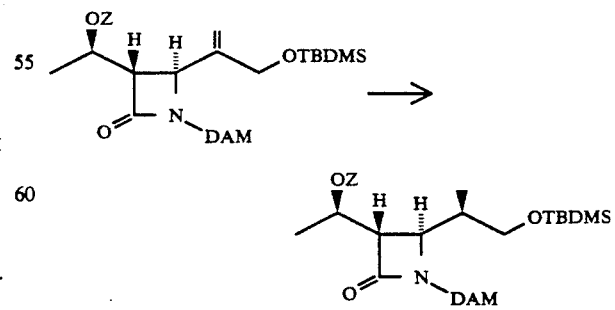

To a solution of (3S,4S)-4-(1-t-butyldimethylsilyloxymethylethenyl)-3-(1-(R)-benzyloxycarbonyloxyethyl)-1-di(p-anisyl)methyl-2-azetidinone (20 g) in acetonitrile (200 ml), there were added 5% platinium on activated carbon (4.0 g) and water (4 ml) under nitrogen atmosphere. The mixture was stirred at 10° C. in a hydrogen gas flow until 2.2 equivalents of hydrogen had been taken up. The catalyst was removed by filtration and washed with ethyl acetate. The filtrate and the washings were combined together and concentrated in vacuo to give (3S,4S)-4-(1-t-butyldimethylsilyloxymethylethyl)-3-(1-(R)-benzyloxycarbonyloxyethyl)-1-di-(p-anisyl)methyl-2-azetidinone as an oil.

High performance liquid chromatography (HPLC) [Lichrosorb$^R$ RP-18], eluting with 85% acetonitrile/water (1 ml/min) and NMR spectra indicated that this product was a mixture of 4-(1-(R)-t-butyldimethylsilyloxyethyl) compound and the corresponding (S)-compound in a ratio of 7.7:1. The above mixture was recrystallized from a mixture of n-hexane and ethyl acetate (10 : 1) to yield the (R)-compound. m.p., 78°–81° C.

NMR δ (CDCl$_3$): 0.01 (6H, s), 0.87 (9H, s), 1.40 (3H, d, J=6 Hz), 3.31 (1H, dd, J=2.2 and 7.0 Hz), 3.44 (2H, d, J=5.3 Hz), 3.73 (3H, s), 3.76 (3H, s), 5.07 (1H, m), 5.17 (2H, s), 7.38 (5H, s).

REFERENCE EXAMPLE 2-9

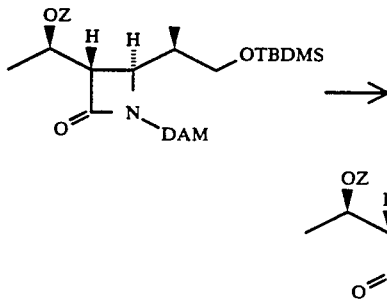

To a solution of (3S,4R)-4-(1-(R)-t-butyldimethylsilyloxymethylethyl)-3-(1-(R)-benzyloxycarbonyloxyethyl)-1-di(p-anisyl)methyl-2-azetidinone (20 g) in dry dichloromethane (200 ml), there were added 1,3-dimethoxybenzene (7.8 g) and boron trifluoride etherate (23 g) at 10°–20° C., and the resultant mixture was stirred at room temperature for 3 hours, followed by heating under reflux for 3–5 hours. The reaction mixture was cooled down to 10°–15° C., washed successively with brine (200 ml×2), 2.5% aqueous sodium bicarbonate solution (200 ml) and brine (200 ml) and dried over anhydrous sodium sulfate. After filtration, the filtrate was concentrated in vacuo to give an oily residue, which was purified by silica gel chromatography to yield (3S,4S)-4-(1-(R)-hydroxymethylethyl)-3-(1-(R)-benzyloxycarbonyloxyethyl)-2-azetidinone.

IR ν$_{max}^{neat}$ (cm$^{-1}$): 3350, 1750, 1740, 1455, 1382, 1260, 1030.

NMR δ (CDCl$_3$) 0.95 (3H, d, J=7.0 Hz), 1.48 (3H, d, J=6.5 Hz), 3.14 (1H, dd, J=2 and 9 Hz), 3.55 (1H, d, J=2 Hz), 5.15 (2H, s), 6.05 (1H, broad, s), 7.37 (5H, s).

REFERENCE EXAMPLE 2-10

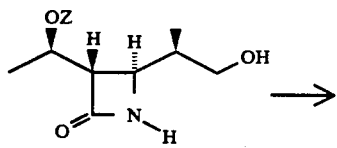

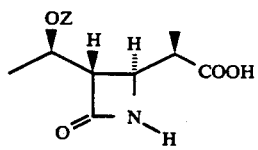

A solution of (3S,4S)-4-(1-(R)-hydroxymethylethyl)-3-(1-(R)-benzyloxycarbonyloxyethyl)-2-azetidinone (6.1 g) in acetone (60 ml) was treated with the Jones reagent, prepared from chromium trioxide (2.78 g), 98% sulfuric acid (4.4 g) and water (8.1 ml), at 10°–20° C. for 1 hour. The reaction mixture was quenched with isopropanol (0.5 ml) at 10°–20° C. for 15 minutes, diluted with ethyl acetate (122 ml) and washed with water (135 ml). The aqueous layer was separated from the organic layer and extracted with ethyl acetate (61 ml). The ethyl acetate extracts and the organic layer were combined together and extracted with 5% aqueous sodium bicarbonate solution (30 ml). The extract was washed with dichloromethane (60 ml) and acidified with 10% hydrochloric acid solution (20 ml) with ice-cooling. The acidic solution was extracted twice with dichloromethane (60 ml). The extracts were washed with brine and dried over anhydrous sodium sulfate. After filtration, the filtrate was concentrated in vacuo to give (3S,4S)-4-(1-(R)-carboxyethyl)-3-(1-(R)-benzyloxycarbonyloxyethyl)-2-azetidinone.

IR ν$_{max}^{neat}$ (cm$^{-1}$): 3270, 1740, 1460, 1385, 1270, 750.

NMR δ (CDCl$_3$) 1.19 (3H, d, J=7.0 Hz), 1.40 (3H, d, J=6.2 Hz), 2.67 (1H, m), 3.22 (1H, broad, d, J=7.5 Hz), 3.84 (1H, broad, d, J=5.5 Hz), 5.14 (2H, s), 6.57 (1H, broad, s), 7.35 (5H, s), 7.63 (1H, broad, s).

REFERENCE EXAMPLE 2-11

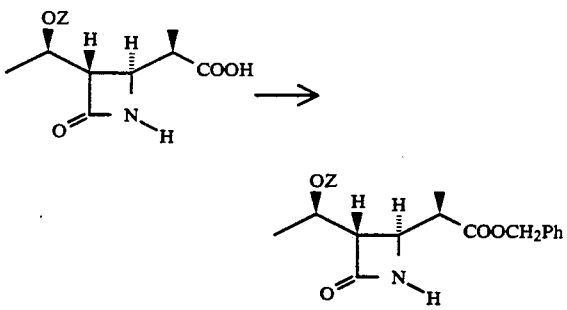

To a solution of 4-(1-(R)-carboxyethyl)-3-(1-(1R)-benzyloxyethyl)azetidin-2-one (51.69 g) in acetone (510 ml), there were added anhydous potassium carbonate (89.0 g) and benzyl bromide (30.3 g), followed by stirring at 60° C. for 1.5 hours. The reaction mixture was cooled to room temperature and filtered off to remove insoluble materials. The filtrate and the washings were combined and evaporated. The residue was purified by silica gel chromatography to give (3S,4S)-3-[(1R)-1-benzyloxycarbonyloxyethyl]-4-[(1R)-1benzyloxycarbonylethyl]azetidin-2-one.

IR ν$_{max}^{neat}$ (cm$^{-1}$): 1760 (sh), 1735, 1450, 1380, 1260, 1155.

NMR δ (CDCl$_3$) 1.22 (3H, d, J=6.9 Hz), 1.39 (3H, d, J=6.3 Hz), 2.71 (1H, q, J=6.9 Hz), 3.19 (1H, dd, J=2.0 and 7.9 Hz), 3.83 (1H, dd, J=2.0 and 6.3 Hz), 5.92 (1H, s).

REFERENCE EXAMPLE 3

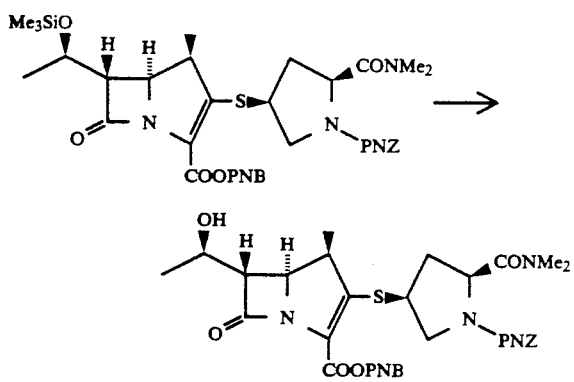

To a solution of (4R,5S,6S,8R,2'S,4'S)-p-nitrobenzyl-3-[4-(1-p-nitrobenzyloxycarbonyl-2-dimethylaminocarbonylpyrrolidinyl)thio]-4-methyl-6-(1-trimethylsilyloxyethyl)-1-azabicyclo[3.2.0]hept-2-en-7-one-2-carboxylate (1.0 g) in dry tetrahydrofuran (10 ml), there was added a phosphate buffer solution (pH 3; 8 ml), and the resultant mixture was vigorously stirred at room temperature for 2.5 hours. The reaction mixture was diluted with ethyl acetate (50 ml), washed with brine, dried over magnesium sulfate and evaporated in vacuo to give (4R,5S,6S,8R,2'S,4'S)-p-nitrobenzyl-3-[4-(1-p-nitrobenzyloxycarbonyl-2-dimethylaminocarbonylpyrrolidinyl)thio]-4-methyl-6-(1-hydroxyethyl)-1-azabicyclo[3.2.0]hept-2-en-7-one-2-carboxylate.

IR $\nu_{max}^{neat}$ (cm$^{-1}$): 1760, 1705, 1645, 1520, 1402, 1342, 1135, 1110.

NMR δ (CDCl$_3$) 1.30 (3H, d, J=7.0 Hz), 1.35 (3H, d, J=6.5 Hz), 2.99 (3H, s), 3.02 (3H, d, J=15 Hz), 5.21 (2H, s), 5.20 and 5.43 (2H, ABq, J=14 Hz), 7.51 (2H, d, J=8.5 Hz), 7.64 (2H, d, J=8.5 Hz), 8.20 (4H, d, J=8.5 Hz).

REFERENCE EXAMPLE 4

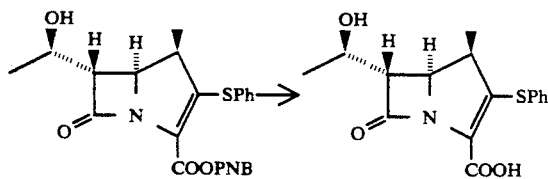

To solution of (4R,5S,6S,8R)-3-phenylthio-4-methyl-6-(1-hydroxyethyl)-1-azabicyclo[3.2.0]hept-2-en-7-one-2-carboxylic acid p-nitrobenzyl ester (37 mg) in tetrahydrofuran (2 ml), a morpholinopropanesulfonic acid buffer solution (pH 7.0; 2 ml) was added, and the resultant mixture was subjected to hydrogenation at room temperature in the presence of 10% palladium-carbon (56 mg) under atmospheric pressure for 4.5 hours. After filtration, the filtrate was stirred under reduced pressure to remove tetrahydrofuran. The filtrate was washed with methylene chloride and stirred again under reduced pressure to remove any organic solvent. The residue was purified by polymer chromatography (CHP-20P), and the fractions eluted with 2% and 5% tetrahydrofuran-water gave (4R,5S,6S,8R)-3-phenylthio-4-methyl-6-(1-hydroxyethyl)-1-azabicyclo[3.2.0]hept-2-en-7-one-2-carboxylic acid.

UV $\lambda_{max}^{HO}$ (nm): 306.

IR $\nu_{max}^{KBr}$ (cm$^{-1}$): 3425 (broad), 1745, 1595, 1400.

NMR δ (D2O)(ppm) 0.90 (3H, d, J=7.3 Hz), 1.18 (3H, d, J=6.3 Hz), 3.00 (1H, m), 3.32 (1H, dd, J=2.6 and 5.9 Hz), 4.09 (1H, dd, J=2.6 and 9.2 Hz), 4.16 (1H, m), 7.3–7.6 (5H, m).

EXAMPLE 7-1

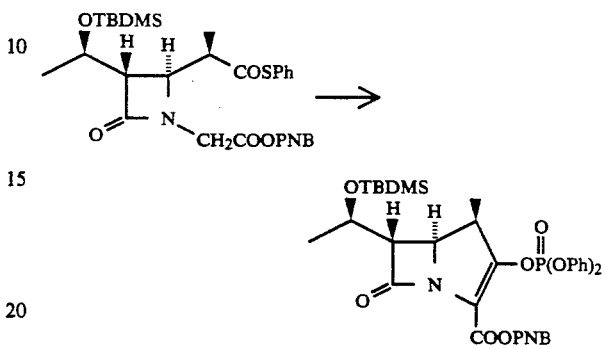

A solution of (3S,4S)-3-[(1R)-1-t-butyldimethylsilyloxyethyl]-4-[(1R)-1-phenylthiocarbonylethyl]-1-p-nitrobenzyloxycarbonylmethyl-2-azetidinone (117 mg) in a mixture of dry toluene and dry tetrahydrofuran (1:1) (1.2 ml) was dropwise added to a suspension of sodium hydride (22 ml; 50% in oil) in a mixture of dry toluene and dry tetrahydrofuran (1:1) (0.2 ml) at −20° C., followed by stirring at the same temperature for 1 hour. A 2M solution (0.1 ml) of iodomethane in tetrahydrofuran was added thereto, and stirring was continued for 30 minutes. A solution of diphenylchlorophosphate (56 ml) in dry toluene (0.1 ml) was added to the mixture at the same temperature, followed by stirring for 1.5 hours. The resultant mixture was diluted with ethyl acetate (20 ml), washed with brine, dried over a mixture of magnesium sulfate and potassium carbonate (10:1) and evaporated in vacuo to give an oily residue, which was purified by silica gel chromatography to obtain (4R,5R,6S,8R)-p-nitrobenzyl-3-diphenylphosphoryloxy-4-methyl-6-(1-t-butyldimethylsilyloxyethyl)-1-azabicyclo[3.2.0]hept-2-en-7-one-2-carboxylate (115 mg).

IR $\nu_{max}^{neat}$ (cm$^{-1}$): 1775, 1725, 1630, 1585, 1518, 1482, 1340, 1285, 1185, 1160, 938, 825, 770.

NMR δ (CDCl$_3$) 0.06 (3H, s), 0.07 (3H, s), 0.86 (9H, s), 1.20 (3H, d, J=7.9 Hz), 1.23 (3H, d, J=6.3 Hz), 3.29 (1H, dd, J=3.0 and 6.0 Hz), 3.43 (1H, m), 4.22 (2H, m), 5.28 (2H, ABq, J=13.5 Hz), 7.56 (2H, d, J=8.9 Hz), 8.14 (2H, d, J=8.9 Hz).

EXAMPLE 7-2

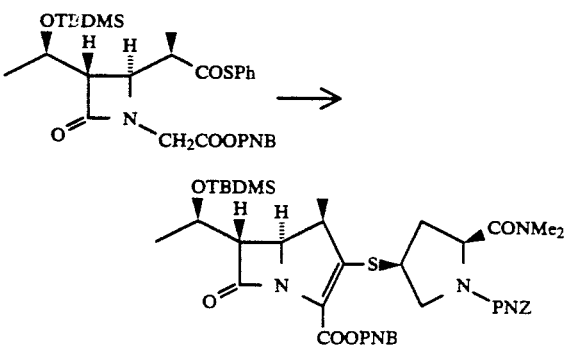

A solution of (3S,4S)-3-[(1R)-1-t-butyldimethyl-silyloxyethyl]-4-[(1R)-1-phenylthiocarbonylethyl]-1-p-nitrobenzyloxycarbonylmethyl-2-azetidinone (415 mg) in a mixture of dry toluene and dry tetrahydrofuran (4:1) (4 ml) was dropwise added to a suspension of sodium hydride (75 ml; 50% in oil) in a mixture of dry toluene and dry tetrahydrofuran (4:1) (0.75 ml) at −20° C., followed by stirring at the same temperature for 1 hour. A 0.5 M solution (1.49 ml) of iodomethane in tetrahydrofuran was added thereto, and stirring was continued for 30 minutes. A solution of diphenyl chlorophosphate (218.5 mg) in dry toluene (2.2 ml) was added to the mixture at the same temperature, followed by stirring for 2 hours. Thereafter, (2S,4S)-1-p-nitrobenzyloxycarbonyl-2-dimethylaminocarbonyl-4-mercaptopyrrolidine (237.5 mg) and sodium hydride (32.3 mg; 50% in oil) were added thereto, and stirring was continued for 2 hours. The resultant mixture was diluted with ethyl acetate (50 ml), washed with brine, dried over magnesium sulfate and evaporated in vacuo to give an oily residue, which was purified by silica gel chromatography to obtain (4R,5S,6S,8R,2'S,4'S)-p-nitrobenzyl-3-[4-(1-p-nitrobenzyloxycarbonyl-2-dimethylaminocarbonylpyrrolidinyl)thio]-4-methyl-6-(1-t-butyldimethylsilyloxyethyl)-1-azabicyclo[3.2.0]hept-2-en-7-one-2-carboxylate carboxylate (329 mg).

IR $\nu_{max}^{neat}$ (cm$^{-1}$): 1775, 1715, 1660, 1610, 1525, 1400, 1345, 1210, 1140, 1110, 835, 755.

EXAMPLE 7-3 (FOR COMPARISON)

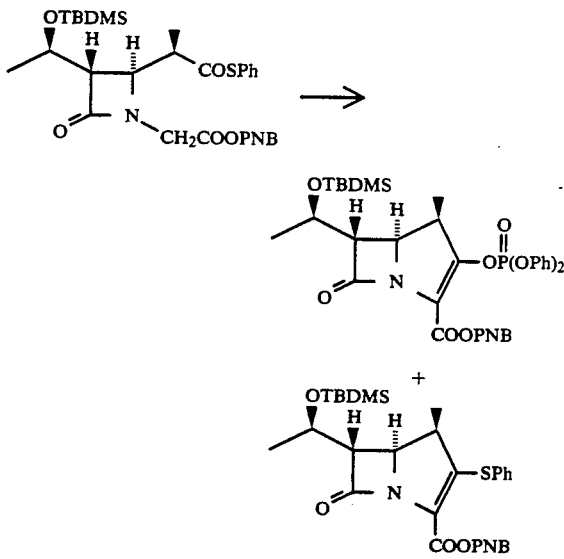

A solution of (3S,4S)-3-[(1R)-1-t-butyldimethyl-silyloxyethyl]-4-[(1R)-1-phenylthiocarbonylethyl]-1-p-nitrobenzyloxycarbonylmethyl-2-azetidinone (69 mg) in dry toluene (0.6 ml) was dropwise added to a suspension of sodium hydride (12.5 ml; 50% in oil) in dry tetrahydrofuran under ice-cooling, and the suspension was stirred for 30 minutes. Diphenyl chlorophosphate (67 mg) was added thereto under ice-cooling, followed by stirring for 1 hour. The resultant mixture was diluted with ethyl acetate (10 ml), washed with brine, dried over a mixture of magnesium sulfate and potassium carbonate (10:1) and evaporated in vacuo to give an oily residue, which was purified by silica gel chromatography to obtain (4R,5S,6S,8R)-p-nitrobenzyl-3-phenylthio-4-methyl-6-(1-t-butyldimethylsilyloxyethyl)-1-azabicyclo-3.2.0]hept-2-en-7-one-2-carboxylate (37 mg) (Compound A) and (4R,5R,6S,8R)-p-nitrobenzyl-3-diphenylphosphoryloxy)-4-methyl-6-(1-t-butyldimethylsilyloxyethyl)-1-azabicyclo-3.2.0]hept-2-en-7-one-2-carboxylate (34 mg) (Compound B).

Compound A

IR $\nu_{max}^{neat}$ (cm$^{-1}$): 1765, 1707, 1522, 1378, 1350, 340, 1140.

NMR δ (CDCl$_3$) 0.06 (6H, s), 0.84 (9H, s), 0.95 (3H, d, J=7.3 Hz), 1.17 (3H, d, J=6.3 Hz), 3.06 (1H, m), 3.19 (1H, dd, J=2.9 and 5.0 Hz), 4.22 (2H, m), 5.40 (2H, ABq, J=13.9 Hz), 7.3–7.6 (5H, m), 7.69 (2H, d, J=8.9 Hz), 8.23 (2H, d, J=8.9 Hz).

Compound B

The IR and NMR spectra data were identical to those of the compound obtained as in Exmaple 7-1.

EXAMPLE 8

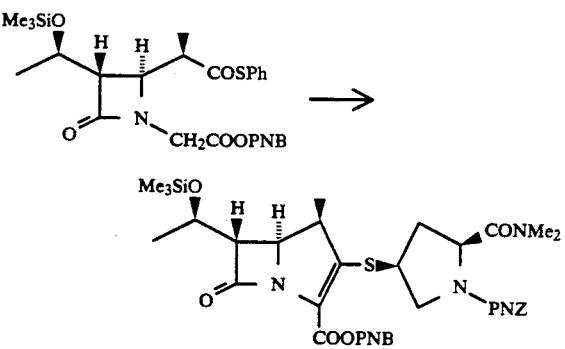

In the same manner as in Example 7-2 but replacing the starting material by (3S,4S)-3-[(1R)-1-trimethyl-silyloxyethyl-9 -4-[(1R)-1-phenylthiocarbonylethyl]-1-p-nitrobenzyloxycarbonylmethyl-2-azetidinone, there was obtained (4R,5S,6S,8R,2'S,4'S)-p-nitrobenzyloxycarbonyl-2-dimethylaminocarbonylpyrrolidinyl)thio]-4-methyl-6-(1-trimethylsilyloxyethyl)-1-azabicyclo[3.2.0]hept-2-en-7-one-2-carboxylate.

IR $\nu_{max}^{neat}$ (cm$^{-1}$): 1765, 1705, 1650, 1600, 1512, 1395, 1335, 1200, 1130, 1100, 840, 740.

EXAMPLE 9

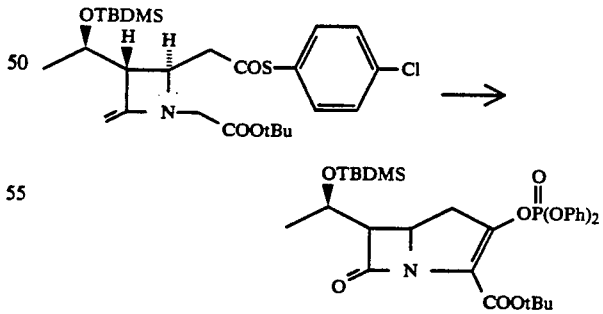

To a solution of (3S,4S)-3-[(1R)-1-t-butyldimethyl-silyloxyethyl]-4-p-chlorophenylthiocarbonylmethyl-1-t-butoxycarbonylmethyl-2-azetidinone (110 mg) in dry tetrahydrofuran (0.5 ml), there was added a 0.5 M solution (0.4 ml) of lithium bis(trimethylsilyl)amide in tetrahydrofuran under nitrogen stream at −70° C., followed by stirring at the same temperature for 15 minutes. Allyl bromide (30 mg) was added thereto, and stirring was continued at −70° C. to −30° C. for 20 minutes. Diisopropylethylamine (35 mg) and then a solution of diphenyl chlorophosphate (60 mg) in dry acetonitrile (1.1 ml) were added to the mixture at −30° C., followed by stirring for 4 hours. The resultant mixture was diluted with ethyl acetate (15 ml), washed with 0.1M phosphate buffer (pH, 6.0), dried over a mixture of magnesium sulfate and potassium carbonate (10:1) and evaporated in vacuo to give an oily residue, which was purified by silica gel chromatography to obtain (5R,6S,8R)-t-butyl-3-diphenylphosphoryloxy-6-(1-t-butyldimethylsilyloxyethyl)-1-azabicyclo[3.2.0]hept-2-en-7-one-2-carboxylate (90 mg). Yield, 71%.

IR $v_{max}^{neat}$ (cm$^{-1}$): 1775, 1712, 1630, 1582, 1480, 1360, 1285, 1180, 1065, 1005, 960, 898, 830, 770.

NMR δ (CDCl$_3$) 0.06 (6H, s), 0.87 (9H, s), 1.21 (3H, d, J=6.0 Hz), 1.49 (9H, s), 3.08–3.16 (3H, m), 4.09 (1H, dt, J=3.0 and 9.2 Hz), 4.19 (1H, quintet, J=6.0 Hz).

What is claimed is:

1. A process for preparing carbapenem compounds of the formula:

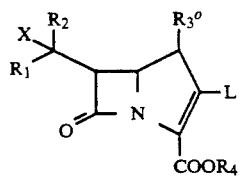
(IX)

wherein $R_1$ and $R_2$ are, the same or different, each a hydrogen atom or a lower alkyl group, $R_3^0$ is a lower alkyl group having a beta-configuration, $R_4$ is a carboxyl-protecting group, X is a hydrogen atom or a protected hydroxyl group and L is an activated hydroxyl group, which comprises subjecting a compound of the formula:

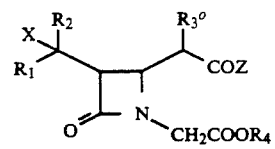
(I-8°)

wherein $R_1$, $R_2$, $R_3^0$, $R_4$ and X are each as defined above and COZ is a protected thiolcarboxyl group to (a) treatment with a base, (b) treatment with an alkylating or acylating agent for catching of the residue $Z^-$ and (c) treatment with a hydroxyl-activating agent in order, said treatments (a), (b) and (c) being carried out without isolation of the intermediates as produced.

2. The process according to claim 1, wherein $R_3^0$ is a methyl group.

3. The process according to claim 1, wherein said alkylating or acylating agent in step (b) is selected from the group consisting of iodomethane, iodopropane, allyl bromide, benzyl bromide and methyl p-toluenesulfonate.

4. A process for preparing carbapenem compounds of the formula:

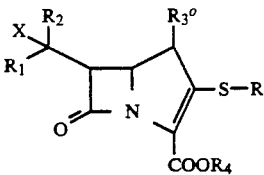
(VII)

wherein R is an organic group, $R_1$ and $R_2$ are, the same or different, each a lower alkyl group, $R_3^0$ is a hydrogen atom or a lower alkyl group having a beta-configuration, $R_4$ is a carboxyl-protecting group and X is a hydrogen atom or a protected hydroxyl group, which comprises subjecting a compound of the formula:

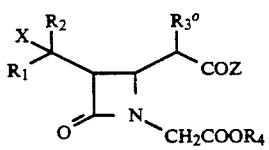
(I-8°)

wherein $R_1$, $R_2$, $R_3^0$, $R_4$ and X are each as defined above and COZ is a protected thiolcarboxyl group to (a) treatment with a base, (b) treatment with an alkylating or acylating agent for catching of the residue $Z^-$ and (c) treatment with a hydroxyl-activating agent in order, followed by (d) reacting the resulting product of the formula:

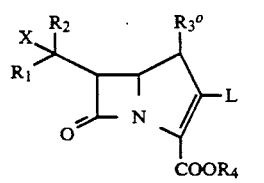
(IX)

wherein $R_1$, $R_2$, $R_3^0$, $R_4$ and X are each as defined above and L is an activated hydroxyl group with a compound of the formula:

HSR (X)

wherein R is as defined above in the presence of a base or with a salt of the compound (X) with the base, said treatments (a), (b) and (c) or (a), (b), (c) and (d) being carried out without isolation of the intermediates as produced.

5. The process according to claim 4, wherein $R_3^0$ is a methyl group.

6. The process according to claim 4, wherein said alkylating or acylating agent in step (b) is selected from the group consisting of iodomethane, iodopropane, allyl bromide, benzyl bromide and methyl p-toluenesulfonate.

7. The process of claim 1, wherein in step (a) treatment of the compound of Formula I-8° the base is present in an amount of from 1.5 to 3 equivalents to the compound of Formula I-8°.

8. The process of claim 7, wherein the step (a) treatment of the compound of Formula I-8° with the base occurs at a temperature of from −75° to 50° C.

9. The process of claim 7, wherein the base is a metal salt of an amine, a metal salt of an alcohol, an alkali metal hydride or sodium methylsulfinylmethide.

10. The process of claim 1, wherein the step (c) hydroxyl-activating agent is an active esterifying agent which is present in an amount of from 1 to 1.5 equivalents to the compound of Formula I-8°.

11. The process of claim 10, wherein the step (c) treatment of the compound of Formula I-8° with the active esterifying agent occurs at a temperature of from −78° to 60°.

12. The process of claim 10, wherein the step (c) treatment of the compound of Formula I-8° with the active esterifying agent occurs at a temperature of from −40° to 10° C.

13. The process of claim 4, wherein in the step (a) treatment of the compound of Formula I-8° the base is present in an amount of from 1.5 to 3 equivalents to the compound of Formula I-8°.

14. The process of claim 13, wherein the step (a) treatment of the compound of Formula I-8° with the base occurs at a temperature of from −75° to 50° C.

15. The process of claim 13, wherein the base is a metal salt of an amine, a metal salt of an alcohol, an alkali metal hydride or sodium methylsulfinylmethide.

16. The process of claim 4, wherein the step (c) hydroxy-activating agent is an active esterifying agent which is present in an amount of from 1 to 1.5 equivalents to the compound of Formula I-8°.

17. The process of claim 16, wherein the step (c) treatment of the compound of Formula I-8° with the active esterifying agent occurs at a temperature of from −78°0 to 60° C.

18. The process of claim 16, wherein the step (c) treatment of the compound of Formula I-8° with the active esterifying agent occurs at a temperature of from −40° to 10° C.

19. The process of claim 4, wherein the compound of Formula X is present in an amount of 1 to 2 equivalents of the amount of the compound of Formula I-8°.

20. The process of claim 1, wherein the alkylating or acylating agent is utilized in an amount sufficient for catching the residue Z.

* * * * *